(12) United States Patent
Frohberg

(10) Patent No.: US 6,590,141 B1
(45) Date of Patent: Jul. 8, 2003

(54) NUCLEIC ACID MOLECULES FROM PLANTS ENCODING ENZYMES WHICH PARTICIPATE IN STARCH SYNTHESIS

(75) Inventor: Claus Frohberg, Berlin (DE)

(73) Assignee: Aventis CropScience GmbH, Frankfurt (DE)

( * ) Notice: Subject to any disclaimer, the term of this patent is extended or adjusted under 35 U.S.C. 154(b) by 13 days.

(21) Appl. No.: 09/638,524

(22) Filed: Aug. 11, 2000

(30) Foreign Application Priority Data

Aug. 11, 1999 (DE) .......................... 199 37 348

(51) Int. Cl.⁷ .................. C12N 15/29; C12N 15/82; C12N 5/04; A01H 5/00; C12P 19/04
(52) U.S. Cl. .................. 800/284; 800/278; 800/286; 800/320.1; 435/69.1; 435/101; 435/320.1; 435/419; 435/468; 536/23.6
(58) Field of Search .................. 536/23.6; 435/69.1, 435/468, 320.1, 419, 101; 800/278, 284, 320.1, 286

(56) References Cited

U.S. PATENT DOCUMENTS 6,130,367 A    10/2000   Kossmann et al.

FOREIGN PATENT DOCUMENTS

| CA | 2242398 | 7/1997 |
|---|---|---|
| CA | 2255538 | 11/1997 |
| DE | 196 19 918 | 11/1997 |
| DE | 196 53 176 | 6/1998 |
| EP | 0 779 363 A2 | 6/1997 |
| WO | WO 96/15248 | 5/1996 |
| WO | WO 97/263362 | 7/1997 |
| WO | WO 98/27212 | 6/1998 |
| WO | WO 99/24575 | 5/1999 |

OTHER PUBLICATIONS

Nakatani et al. Jpn. J. Crop Sci. 61(3): 463–468, 1992.*
Kossmann et al. Progress Biotechnol. 10:271–278, 1995.*
Sasaki, T. Accession No. C99345, 1996.*
Database Accession No. C99345 published Oct. 16, 1998, also referred to as XP 002163786.
Database Accession No. AI94842 published Aug. 23, 1999, also referred to as XP 002163787.
Cao, Heping et al, "Identification of the Soluble Starch Synthase Activities of Maize Endosperm", Plant Physiology, May 1999, vol. 120, pp. 205–215, No. 1.

* cited by examiner

Primary Examiner—David T. Fox
(74) Attorney, Agent, or Firm—Frommer Lawrence & Haug LLP

(57) ABSTRACT

Nucleic acid molecules are described which encode enzymes which participate in starch synthesis in plants. These enzymes are a new isoform of starch synthase. There are furthermore described vectors for generating transgenic plant cells and plants which synthesize a modified starch. There are furthermore described methods for the generation of these transgenic plant cells and plants, and methods for producing modified starches.

19 Claims, 1 Drawing Sheet

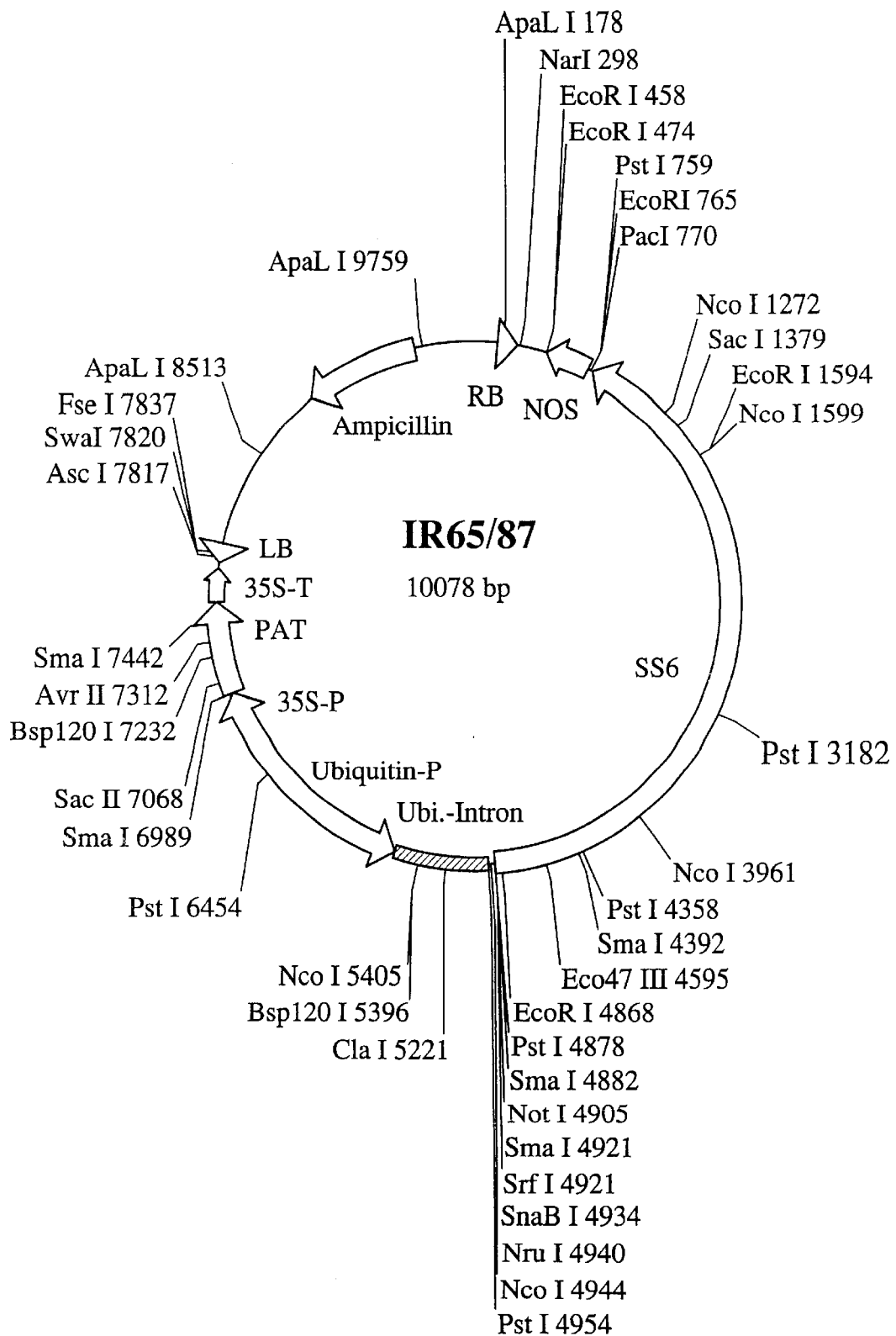

NUCLEIC ACID MOLECULES FROM PLANTS ENCODING ENZYMES WHICH PARTICIPATE IN STARCH SYNTHESIS

FIELD OF THE INVENTION

The invention furthermore relates to vectors and to host cells transformed with the described nucleic acid molecules or vectors, in particular plant cells and plants which can be regenerated from these.

There are also described methods for the generation of transgenic plant cells and plants which, owing to the introduction of DNA molecules encoding a starch synthase, synthesize a starch whose properties are altered. The present invention also relates to the starch which can be obtained from the plant cells and plants according to the invention, and to processes for the production of this starch.

Bearing in mind the recently increasing importance of plant constituents as renewable raw materials, it is one of the tasks of biotechnology research to attempt to adapt these plant raw materials to the demands of the processing industry. Thus, to make possible the use of renewable raw materials in as many fields of application as possible, it is necessary to make available a great variety of materials. Not only oils, fats and proteins, but also polysaccharides, constitute important renewable raw materials from plants. A pivotable position in the polysaccharides is taken up not only by cellulose, but also by starch, which is one of the most important storage materials in higher plants. In this context, maize is one of the most interesting plants, since it is the most important crop plant worldwide for starch production.

The polysaccharide starch is a polymer of chemically uniform base units, the glucose molecules. However, it is a highly complex mixture of different forms of molecules which differ with regard to their degree of polymerization and the occurrence of branchings in the glucose chains. Starch is therefore no uniform raw material. In particular, we differentiate between amylose starch, an essentially unbranched polymer of α-1,4-glycosidically linked glucose molecules, and amylopectin starch, which, in turn, constitutes a complex mixture of differently branched glucose chains. Other branchings are generated by the occurrence of additional α-1,6-glycosidic linkages. In typical plants used for starch production such as, for example, maize or potatoes, the starch synthesized consists of approx. 20%–25% of amylose starch and approx. 75%–80% of amylopectin starch.

To allow as broad an application of starch as possible, it appears desirable to provide plants which are capable of synthesizing modified starch which is particularly suitable for various purposes. One possibility of providing such plants is—besides plant-breeding measures—the targeted genetic alteration of the starch metabolism of the starch-producing plants by recombinant methods. However, a prerequisite for this is the identification and characterization of the enzymes which participate in starch synthesis and/or starch modification, and the isolation of the relevant DNA molecules which encode these enzymes.

The biochemical synthetic pathways which lead to the synthesis of starch are essentially known. In plant cells, starch synthesis takes place in the plastids. In photosynthetically active tissues, these are the chloroplasts, in photosynthetically inactive, starch-storing tissues, the amyloplasts.

The most important enzymes which participate in starch synthesis are the starch synthases and the branching enzymes. Amongst the starch synthases, various isoforms have been described, all of which catalyze a polymerization reaction by transferring a glucosyl residue from ADP-glucose to α-1,4-glucans. Branching enzymes catalyze the introduction of α-1,6-branchings into linear α-1,4-glucans. Two classes of starch synthases can be distinguished: the granule-bound starch synthases (GBSS) and the soluble starch synthases (SS). However, this distinction is not clear-cut in each individual case, since some of the starch synthases are present both in granule-bound form and in soluble form (Denyer et al., Plant J. 4 (1993), 191–198; Mu et al., Plant J. 6 (1994), 151–159).

Besides the class of the granule-bound starch synthases, GBSSI, at least three different isoforms have been described in maize plants within the class of the soluble starch synthases, based on cDNA and amino acid sequence comparisons. Isoform I of starch synthase (SSI) includes genes, which, in maize, encode an approx. 76 kDa protein zSSI (Mu et al., Plant J 6, (1994), 151–159) and which have as yet only been described for monocotyledonous plants such as, for example, for rice (Baba et al., Plant Physiol. 103, (1993), 565–573), are expressed mainly in the endosperm. As a rule, these proteins are stimulated by citrate and are independent of so-called primer molecules.

In contrast, isoform II starch synthases (=SSII) are, as a rule, dependent on primer molecules and show the highest sequence homology with the SSII Isoforms—some of which used to be termed GBSSII—from pea (Dry et al., Plant J. 2, (1992), 193–202) and potato (Edwards et al., Plant J 8, (1995), 283–294).

When considering the maize SSII, a distinction must be made between the genes, or cDNAs, which are termed zSSIIa and zSSIIb in the literature (Ham et al., Plant Mol. Biol. 37, (1998), 639–649; Imparl-Radosevich, Arch. Biochem. Biophys. 362, (1999), 131–138), and the so-called SSII protein, an approx. 180 kDa protein (molecular weight determined by means of gel filtration (Mu et al., Plant J. 6, (1994), 151–159)) from maize endosperm, whose name is based on earlier biochemical studies (Boyer and Preiss, Plant Physiol. 67, (1981), 1141–1145; Mu et al., Plant J. 6, (1994), 151–159). The question of which gene actually corresponds to these 180 kDa proteins is currently not conclusively answered (Imparl-Radosevich, Arch. Biochem. Biophys. 362, (1999), 131–138). Cao et al. (Plant Physiol. 120, (1999), 205–215) propose the so-called du1 gene as the gene which corresponds to the 180 kDa protein.

The third class of starch synthase genes which has been described to date, termed SSIII, encode, in potatoes, an 139 kDa protein (Abel et al., Plant J. 10, (1996), 981–991; Marshall et al., Plant Cell 8, (1996), 1121–1135), which amount to 80% of the total starch synthase activity in potato tubers. Since certain sequence regions of the C-terminus are highly conserved in comparison with the potato SSIII amino acid sequence, it was proposed to rename the maize gene originally termed du1 gene "zSSIII" (Cao et al., Plant Physiol. 120, (1999), 205–215), the prefix "z" denoting the organism of origin *Zea mays*.

The detailed function in starch synthesis has as yet only been determined for the isoform GBSS I. Plants in which this enzyme activity is greatly or fully reduced synthesize an amylase-free "waxy" starch (Shure et al., Cell 35 (1983), 225–233; Visser et al., Mol. Gen. Genet. 225 (1991), 289–296; WO9211376A1), so that an important role in amylose starch synthesis is attributed to this enzyme. This phenomenon is likewise observed in cells of the green algae *Chlamydomonas reinhardtii* (Delrue et al., J. Bacteriol. 174

(1992), 3612–3620). In Chlamydomonas, it was additionally possible to demonstrate that GBSS I not only participates in amylose synthesis, but also affects amylopectin synthesis. Mutants which have no GBSSI activity lack a particular fraction of the usually synthesized amylopectin, which contains longer-chain glucans.

The functions of the isoforms of the soluble starch synthases remain unclear, it is assumed that the soluble starch synthases together with branching enzymes participate in amylopectin synthesis (see, for example, Ponstein et al., Plant Physiol. 92 (1990), 234–241) and that they play an important role in the regulation of the starch synthesis rate.

Besides maize, soluble starch synthases were also identified in a series of other plant species. For example, soluble starch synthases have been isolated until homogeneous from pea (Denyer and Smith, Planta 186 (1992), 609–617) and potato (Edwards et al., Plant J. 8 (1995), 283–294). It emerged in these cases that the isoform of the soluble starch synthase which is identified as SS II is identical with the granule-bound starch synthase GBSS II (Denyer et al., Plant J. 4 (1993), 191–198; Edwards et al., Plant J. 8 (1995), 283–294). The presence of a plurality of SS isoforms has been described for some other plant species with the aid of chromatographic methods, for example in barley (Tyynelä and Schulman, Physiologia Plantarum 89 (1993) 835–841; Kreis, Planta 148 (1980), 412–416) and wheat (Rijven, Plant Physiol. 81 (1986), 448–453). DNA sequences which encode these proteins have also been described (see, for example, GenBank Acc. No. U48227; Vrinten et al., Mol. Gen. Genet. 261 (3), (1999), 463–471).

To provide further options of altering any starch-storing plant in such a way that it synthesizes a modified starch, it is necessary to identify DNA sequences in each case which encode further isoforms of the starch synthases.

It is therefore an object of the present invention to provide nucleic acid molecules which encode enzymes which participate in starch biosynthesis and with the aid of which it is possible to generate recombinant plants which exhibit an increased or reduced activity of these enzymes, thus resulting in altered chemical and/or physical properties of the starch synthesized in these plants, which is therefore better suited to general and/or specific purposes.

This object is achieved by providing the embodiments described in the patent claims.

SUMMARY OF THE INVENTION

The present invention therefore relates to nucleic acid molecules which encode proteins with the bioactivity of starch synthase or a bioactive fragment of such a protein, such molecules preferably encoding proteins with the amino acid sequence indicated under Seq ID No. 2.

In particular, the invention relates to nucleic acid molecules which comprise the nucleotide sequence indicated under Seq ID No. 1, or part thereof, preferably molecules which encompass the coding region indicated in Seq ID No. 1, or corresponding ribonucleotide sequences.

The invention also relates to nucleic acid molecules which have a sequence which is complementary to all or part of the sequence shown in Seq ID No. 1.

Subject matter of the invention are also nucleic acid molecules which encode a starch synthase or a bioactive fragment thereof and/or whose sequence deviates from the nucleotide sequences of the above-described molecule owing to the degeneracy of the genetic code.

The present invention furthermore relates to nucleic acid molecules which encode a starch synthase or a bioactive fragment thereof and which hybridize with one of the above-described molecules.

DETAILED DESCRIPTION OF THE INVENTION

The nucleic acid molecules according to the invention can be both DNA and RNA molecules. Suitable DNA molecules are, for example, genomic or cDNA molecules. RNA molecules can be, for example, mRNA or antisense-RNA molecules. The present invention therefore also relates to nucleotide sequences of introns which are part of the genomic sequences which correspond to the cDNA sequences indicated under SEQ ID No. 1. Suitable intron sequences can be isolated and identified, for example, using the nucleic acid molecules indicated under SEQ ID No. 1, for example by screening a genomic DNA library.

The term "hybridization" means for the purposes of the present invention hybridization under conventional hybridization conditions, preferably under stringent conditions as they are described, for example, by Sambrook et al., Molecular Cloning, A Laboratory Manual, 2nd Ed. (1989) Cold Spring Harbor Laboratory Press, Cold Spring Harbor, N.Y. "Hybridization" especially preferably means that hybridization takes place under the following conditions:

Hybridization buffer: 2×SSC; 10×Denhardt solution (Ficoll 400+PEG+BSA; ratio 1:1:1); 0.1% SDS; 5 mM EDTA; 50 mM $Na_2HPO_4$;

250 µg/ml herring sperm DNA; 50 µg/ml tRNA; or 0.25 M sodium phosphate buffer pH 7.2;

1 mM EDTA

7% SDS hybridization temperature T=65 to 68° C.

wash buffer: 0.2×SSC; 0.1% SDS wash temperature T=40 to 68° C.

Nucleic acid molecules which hybridize with the nucleic acid molecules according to the invention can be derived, in principle, from any organism (i.e. prokaryotes or eukaryotes, in particular from bacteria, fungi, algae, plants or animal organisms) which has such molecules. They are preferably derived from monocotyledonous or dicotyledonous plants, in particular from useful plants, especially preferably from starch-storing plants, in particular from maize.

Nucleic acid molecules which hybridize with the molecules according to the invention can be isolated, for example, from genomic or from cDNA libraries of various organisms. Alternatively, they can be generated by recombinant methods or synthesized chemically.

Such nucleic acid molecules can be identified and isolated from plants or other organisms using the molecules according to the invention or parts of these molecules or the reverse complements of these molecules, for example by means of hybridization following standard methods (see, for example, Sambrook et al., 1989, Molecular Cloning, A Laboratory Manual, 2nd Ed., Cold Spring Harbor Laboratory Press, Cold Spring Harbor, N.Y.).

Hybridization probes which can be used are, for example, nucleic acid molecules which exactly or essentially have the nucleotide sequence indicated under Seq ID No. 1 or parts of this sequence. The fragments used as hybridization probe can also be synthetic fragments which were prepared with the aid of the customary synthetic techniques and whose sequence essentially agrees with that of a nucleic acid molecule according to the invention. Once genes which hybridize with the nucleic acid sequences according to the invention have been identified and isolated, the sequence must be determined and the properties of the proteins encoded by this sequence analyzed.

The invention furthermore relates to plasmid IR 65/87, which was deposited at the Deutsche Sammlung für Mikroorganismen, Braunschweig, Germany, on Aug. 5, 1999 under the number DSM 12970, and to the nucleic acid molecule contained in the insertion of plasmid IR 65/87 which encodes a protein with the enzymatic activity of a starch synthase. In addition, the present invention relates to fragments of the nucleic acid molecule contained in the insertion of plasmid IR 65/87, preferably to fragments which encompass the encoding region or part thereof. Furthermore, the present invention also relates to nucleic acid molecules which hybridize with the nucleic acid molecule contained in the insertion of plasmid IR 65/87, and to nucleic acid molecules which have a sequence which is complementary to all or part of the insertion of the nucleic acid molecule contained in plasmid IR 65/87. In addition, the present invention relates to nucleic acid molecules whose nucleotide sequence deviates in comparison with the nucleic acid molecules of the insertion of plasmid IR 65/87, owing to the degeneracy of the genetic code.

The present invention also relates to fragments and allelic variants of the above-described nucleic acid molecules according to the invention.

Fragments are to be understood as meaning parts of the nucleic acid molecules according to the invention which encode a protein according to the invention or parts of this protein and which are, as a rule, oligo- or polynucleotides composed of approximately 25 to 150, preferably of at least 150, especially preferably at least 500, in particular at least 1000 and especially preferably of at least 3500 nucleotides of the nucleic acid molecules according to the invention.

The term "fragment" is to be understood as meaning in the present context a part of the nucleic acid molecules according to the invention which encodes a part of the protein according to the invention and is functionally active. Furthermore, the fragment may also encode an antisense-mRNA or be contained in a molecule which mediates a cosuppression effect or an in-vivo mutagenesis effect. "Functionally active" means in the present context that the bioactivity of the protein encoded by the nucleic acid molecule according to the invention is either increased or reduced in a plant cell according to the invention.

The allelic variants can be not only naturally occurring variants, but also synthesized variants or variants which have been generated by recombinant DNA technology.

The invention also relates to derivatives of the above-described nucleic acid molecules according to the invention. The term "derivative" means in this context that the sequences of these molecules differ from the sequences of the above-described nucleic acid molecules with regard to one or more positions and have a high degree of homology to these sequences, in particular the coding region of the nucleotide sequence indicated under SEQ ID No. 1. Homology in this context means a sequence identity of at least 50%, in particular an identity of at least 70%, preferably over 85% and especially preferably over 95%. The deviations with regard to the above-described nucleic acid molecules may have been generated by deletion, substitution, insertion or recombination.

"Homology" for the purposes of the present invention means that a functional and/or structural equivalence exists between the nucleic acid molecules in question and the proteins encoded by them. The nucleic acid molecules which are homologous to the above-described molecules and which constitute derivatives of these molecules are, as a rule, variations of these molecules which constitute modifications which exert the same biological function. They may be naturally occurring variations, for example sequences from other organisms, or mutations, it being possible for these mutations to have occurred naturally or to have been introduced by directed mutagenesis.

The proteins encoded by the various variants (fragments, derivatives, allelic variants) of the nucleic acid molecules according to the invention share certain characteristics with the amino acid sequence defined under Seq ID No. 2. These may include, for example, enzyme activity, molecular weight, immunological reactivity, conformation etc., and physical properties such as, for example, the migration behavior in gel electrophoresis, the chromatographic behavior, sedimentation coefficients, solubility, spectroscopic properties, stability, pH optimum, temperature optimum, etc.

Important characteristics of a starch synthase are: i) its localization in the stroma of the plastids of plant cells; ii) its capability of synthesizing linear α-1,4-linked polyglucans using ADP-glucose as substrate. This activity can be determined as described by Denyer and Smith (Planta 186 (1992), 609–617).

The nucleic acid molecules according to the invention can originate from a pro- or eukaryotic organism which expresses the genes described, preferably from plants, in particular from starch-synthesizing or starch-storing plants. These can be both monocotyledonous and dicotyledonous plants. Especially preferred in this context are, for example, cereal species (such as barley, rye, oats, wheat etc.), maize, rice, peas, cassava, potatoes and the like.

The proteins encoded by the nucleic acid molecules according to the invention are an isoform of a plant starch synthase which has previously not been identified and characterized. These proteins have the enzymatic activity of a starch synthase and show significant homology to the potato SSIII (Marshall et al., Plant Cell 8, (1996), 1121–1135) and the maize isoform termed zSSIII (du1) (Cao et al., Plant Physiol. 120, (1999), 205–215) in the region of amino acids 740 to 1170 of the amino acid sequence indicated under SEQ ID No. 2. The proteins encoded by the nucleic acid molecules according to the invention differ from the potato SSIII and the maize zSSIII significantly by their N-terminus. Furthermore, the calculated isoelectric point of the protein indicated under SEQ ID No. 2 differs significantly from the calculated isoelectric points for the potato SSIII and the maize zSSIII. Moreover, the protein indicated under SEQ ID No. 2 has a clearly reduced calculated molecular weight of approx. 132 kDa in comparison with the zSSIII (calculated molecular weight approx. 188 kDa). As opposed to zSSIII, expression of the genes of the isoform according to the invention is greater in young leaves than in the endosperm.

In a further embodiment, the present invention therefore relates to the above-described nucleic acid molecules according to the invention which encode proteins with the bioactivity of a starch synthase, such molecules preferably encoding for proteins which have a homology of at least 50%, preferably of at least 65%, in particular of at least 80% and especially preferably of at least 95% with the amino acid sequence indicated under SEQ ID No. 2 in the N-terminal region. The term "N-terminus" is to be understood as meaning in this context the amino acids 1 to 150, preferably the amino acids 1 to 300, and especially preferably the amino acids 1 to 480 of the amino acid sequence indicated under SEQ ID No. 2.

In a further embodiment of the invention, the nucleic acid molecules according to the invention encode proteins with the bioactivity of a starch synthase, such molecules encoding proteins which have a calculated isoelectric point pI=6.95 pH±1.00 pH, preferably pI=6.95 pH±0.75 pH, especially preferably pI=6.95 pH±0.50 pH.

In a further embodiment, the nucleic acid molecules according to the invention encode proteins with the bioactivity of a starch synthase which have at least one deletion in at least one of the eight sequence motifs which are characteristic of starch synthases and which have been described by Cao et al. (Plant Physiol. 120, (1999), 205–215). The deleted motif is preferably that termed sequence motif VII by Cao et al. (Plant Physiol. 120, (1999), 205–215). In a further embodiment, the nucleic acid molecules according to the invention therefore encode proteins with the bioactivity of a starch synthase which have at least one deletion in one or more of the sequence motifs VII, selected from the group consisting of SHTIYMSDLFIIPSIFEPCGLTQMIAMRYGS (Seq ID No. 3);
SHLIYAGADFILVPSIFEPCGLTQLTAMRYGS (Seq ID No. 4);
SHLIYAGSDFILVPSIFEPCGLTQLVAMRYGT (Seq ID No. 5);
AHQMMAGADVLAVTSRFEPCGLIQLQGMRYGT (Seq ID No. 6);
AHQMMAGADVLAVTSRFEPCGLIQLQGMRYGT (Seq ID No. 7);
AHMITAGADFMLIPSRFEPCGLIQLHAMRYGT (Seq ID No. 8);
AHMITAGADFMLVPSRFEPCGLIQLHAMRYGT (Seq ID No. 9);
AHLIMAGADVLAVPSRFEPCGLIQLQGMRYGT (Seq ID No. 10);
AHKIIAGADFIVIPSRFEPCGLVQLHAMPYGT (Seq ID No. 11);
AHHIMAGADLLAVTSRFEPCGLIQLQGMRYGT (Seq ID No. 12);
AHHIMAGADVLAVTSRFEPCGLIQLQGMRYGT (Seq ID No. 13);
SHRITAGCDILLMPSRFEPCGLNQLYAMQYGT (Seq ID No. 14);
AHRITAGSDILLMPSRFEPCGLNQLYAMSYGT (Seq ID No. 15);
SHRITAGCDILLMPSRFEPCGLNQLYAMRYGT (Seq ID No. 16);
SHRITAGADILLMPSRFEPCALNQLYAMKYGT (Seq ID No. 17);
AHRITAGADIALMPSRFEPCGLNQLYAMAYGT (Seq ID No. 18);
SHRITAGCDILLMPSRFEPCGLNQLYAMQYGT (Seq ID No. 19);
SHRITAGCDILLMPSRFEPCGLNQLYAMQYGT (Seq ID No. 20);
AHRITAGADVLVMPSRFEPCGLNQLYAMAYGT (Seq ID No. 21);
AHRITAGADILLMPSRFEPCGLNQLYAMAYGT (Seq ID No. 22);
ARKLYASSDFILMPSYFEPCGLTQMIGMRYGC (Seq ID No. 23);
AHQIYAGSDMFLMPSKFEPCGLTQLYALRYGC (Seq ID No. 24);
AHQIYAGADLFLIPSLFEPCGLSQMIALRYGT (Seq ID No. 25);
AHQIYAGADLFLIPSLFEPCGLGQLIALQYGA (Seq ID No. 26);
SHRIMGGADVILVPSRFEPCGLTQLYGSKYGT (Seq ID No. 27);
SHLMVAGGDVILVPSRFEPCGLTQLYGLQYGT (Seq ID No. 28) and
AHLIYGMDIIWPSNYEPCGLTQMIGLRYGA (Seq ID No. 29) (cf. sequence motif VII as defined by Cao et al., Plant Physiol. 120, (1999), p. 207, table 1).

Methods for identifying said sequence motifs are known to the skilled worker and may be based on amino acid sequence comparisons with the characteristic sequence motifs VII described by Cao et al (see above).

In a further preferred embodiment of the invention, the nucleic acid molecules according to the invention encode proteins with the function of a starch synthase which has a deletion of at least 2 amino acids, especially preferably of at least 5 amino acids, in particular of at least 10 amino acids and especially preferably of at least 20 amino acids in one or more of the motifs as shown in Seq ID No. 3 to 29. In a further especially preferred embodiment of the invention, said sequence motif VII of the proteins encoded by the above-described nucleic acid molecules according to the invention has the following amino acid sequence: (1)SH—AMRYG-(11), it being possible for positions 3, 4, 5 and 11 of this motif to be occupied by any amino acid. In Seq ID No. 2, sequence motif VII starts at amino acid 1067 (═S) and ends at amino acid 1077 (═S).

In position 3, there is especially preferably an amino acid selected from the group consisting of T, L, M, Q or R. In position 4, there is preferably an amino acid selected from the group consisting of I, L or M. In position 5, there is preferably an amino acid selected from the group consisting of I, Y, M, T or V. In position 11, there is preferably an amino acid selected from the group consisting of S, T, C or A.

The present invention also relates to the use of the above-described nucleic acid molecules according to the invention for screening nucleic acid libraries, in particular cDNA and genomic libraries and/or as hybridization probe. In addition, the present invention also relates to the use of the above-described nucleic acid molecules according to the invention for generating transgenic plant cells or transgenic plants.

Furthermore, the invention relates to vectors, in particular plasmids, cosmids, viruses, bacteriophages and other vectors commonly used in genetic engineering which contain the above-described nucleic acid molecules according to the invention.

In a preferred embodiment, the nucleic acid molecules contained in the vectors are linked to regulatory elements which ensure the transcription and synthesis of translatable RNA in prokaryotic or eukaryotic cells or in the cell-free system. Regulatory elements for expressing the nucleic acid molecules according to the invention in microorganisms (for example E. coli, S. cerevisiae) have been described widely in the literature. Promoters which permit a particularly strong expression of the gene downstream are, for example, the T7 promoter (Studier et al., Methods in Enzymology 185, (1990), 60–89), lacuv5, trp, trp-lacUV5 (DeBoer et al., in: Rodriguez and Chamberlin (Eds), Promoters, Structure and Function; Praeger, N.Y., (1982), 462–481; DeBoer et al, Proc. Natl. Acad. Sci. USA (1983), 21–25), Ip1, rac (Boros et al., Gene 42 (1986), 97–100). As a rule, protein quantities reach their maximum from the middle towards the end of the logarithmic phase of the growth cycle of the microorganisms. Thus, inducible promoters are preferably used for synthesizing proteins. These frequently lead to higher protein yields than constitutive promoters. The use of strong constitutive promoters frequently leads to the loss of energy for other essential cell functions, owing to the constant transcription and translation of a cloned gene, thus slowing down cell growth (Bernard R. Glick/Jack J. Pasternak, Molekulare Biotechnologie [Molecular Biotechnology] (1995), Spektrum Akademischer Verlag GmbH, Heidelberg Berlin Oxford, p. 342.). Thus, to achieve an optimal protein quantity, a two-step process is frequently used. First, the host cells are grown under optimal conditions up to a relatively high cell density. In the second step, transcription is then induced, depending on the type of the promoter employed.

Especially suitable in the present context is a lactose- or IPTG (=isopropyl-β-D-thiogalactopyranoside) inducible tac promoter (deBoer et al., Proc. Natl. Acad. Sci. USA 80 (1983), 21–25). Termination signals for transcription are also described in the literature.

Regulatory elements for expressing the nucleic acid molecules according to the invention in plant cells are described in connection with the plant cells according to the invention.

Expression of the nucleic acid molecules according to the invention in prokaryotic cells, for example in *Escherichia coli* is important insofar as this allows the enzymatic activities of the enzymes encoded by these molecules to be characterized in greater detail. In particular, it is possible to characterize the product synthesized by the enzymes in question in the absence of other enzymes which participate in starch synthesis in the plant cell. This allows conclusions to be drawn of the function which the protein in question has during starch synthesis in the plant cell.

In addition, it is possible to introduce various mutations into the nucleic acid molecules according to the invention by customary techniques of molecular biology (see, for example, Sambrook et al., 1989, Molecular Cloning, A Laboratory Manual, 2nd Ed., Cold Spring Harbor Laboratory Press, Cold Spring Harbor, N.Y.), this leading to the synthesis of proteins with potentially altered biological properties. On the one hand, it is possible to generate deletion mutants in which nucleic acid molecules are generated by progressive deletions starting at the 5'- or at the 3'-end of the coding DNA sequence, which lead to the synthesis of suitably truncated proteins. For example, such deletions at the 5'-end of the nucleotide sequence allow amino acid sequences to be identified which are responsible for the translocation of the enzyme into the plastids (transit peptides). This permits the targeted production of enzymes which, owing to the removal of the sequences in question, are no longer localized in the plastids, but in the cytosol, or which, owing to the addition of other signal sequences, are localized in other compartments.

The exchange of the homologous transit peptide for another transit peptide which mediates localization in the plastids is also feasible. A plastid signal sequence which can be used is, for example, the spinach ferrodoxin:NADP$^+$ oxidoreductase (FNR). This sequence contains the 5' non-translated region and the flanking transit peptide sequence of the cDNA of the plastid protein spinach ferrodoxin:NADP$^+$ oxidoreductase (nucleotides −171 to +165; Jansen et al., Current Genetics 13, (1988), 517–522).

Another plastid signal sequence which can be used is, for example, the transit peptide of the maize waxy protein plus the first 34 amino acids of the mature waxy protein (Klösgen et al., Mol Gen Genet. 217, (1989), 155–161). In addition, the transit peptide of the maize waxy protein (see above) may also be used without the first 34 amino acids of the mature waxy proteins.

On the other hand, the introduction of point mutations into the nucleic acid molecules according to the invention is also feasible in positions where an altered amino acid sequence has an effect on, for example, enzyme activity or enzyme regulation. This allows for example mutants to be generated which have an altered $k_{cat}$ and/or $K_m$ value or which are no longer subject to the regulatory mechanisms via allosteric regulation or covalent modification which are normally present in the cell. Moreover, it is possible to generate mutants which have an altered substrate or product specificity, such as, for example, mutants which use ADP-glucose-6-phosphate instead of ADP-glucose as substrate. Furthermore, it is possible to generate mutants which have an altered activity—temperature profile.

To carry out recombinant manipulations in prokaryotic cells, the nucleic acid molecules according to the invention or parts of these molecules can be introduced into plasmids which permit mutagenesis or sequence modification by the recombination of DNA sequences. Base exchanges may be carried out or natural or synthetic sequences added with the aid of standard methods (cf. Sambrook et al., 1989, Molecular Cloning: A laboratory manual, 2nd Ed., Cold Spring Harbor Laboratory Press, N.Y., USA). To commit the DNA fragments to each other, adapters or linkers may be added to the fragments. Moreover, manipulations may be employed which provide suitable restriction cleavage sites or which remove excess DNA or restriction cleavage sites. Where insertions, deletions or substitutions are suitable, in-vitro mutagenesis, primer repair, restriction or ligation may be used. Analytical methods which are generally carried out are a sequence analysis, a restriction analysis and other methods of biochemistry and molecular biology.

Furthermore, the present invention relates to vectors which contain the above-described nucleic acid molecules according to the invention, the nucleic acid molecules being connected in sense orientation with regulatory elements which ensure the transcription and synthesis of a translatable RNA in pro- or eukaryotic cells.

The meaning of the term "sense orientation" is known to the skilled worker.

In a further embodiment, the invention relates to host cells, in particular prokaryotic or eukaryotic cells, which are transformed with an above-described nucleic acid molecule according to the invention or a vector according to the invention, and cells which are derived from such transformed cells and contain a nucleic acid molecule according to the invention or a vector according to the invention. These are preferably bacterial cells, especially preferably plant cells.

The present invention furthermore relates to a method for generating a host cell, wherein a host cell is genetically modified by introducing a nucleic acid molecule according to the invention and/or a vector according to the invention. The host cell may be of prokaryotic or else eukaryotic origin. The cells are preferably bacterial cells, especially preferably plant cells.

The term "genetically modified" means in connection with the present invention that the host cell, in particular a plant cell, is altered with regard to its genetic information by introducing a nucleic acid molecule according to the invention, and that the presence or the expression of the nucleic acid molecule according to the invention results in a phenotypic change. Phenotypic change in this context preferably means a measurable change in one or more cell functions. For example, genetically modified plant cells according to the invention show a reduced activity of the protein according to the invention or an increased activity of the protein according to the invention.

Subject matter of the invention are furthermore the proteins or bioactive fragments thereof which are encoded by the nucleic acid molecules according to the invention and methods for their production, where a host cell according to the invention is grown under conditions which permit the synthesis of the protein and the protein is subsequently isolated from the cultured cells and/or the culture medium. The characteristic properties of the proteins according to the invention have already been described above in connection with the description of the corresponding nucleic acid molecules according to the invention.

The provision of the nucleic acid molecules according to the invention now allows engagement, with the aid of recombinant methods, in the starch metabolism of plants, in an unprecedented manner and to alter it in such a way that the synthesis of a modified starch results which is altered in comparison with starch synthesized in wild-type plants for example with regard to its physicochemical properties, in particular the amylose/amylopectin ratio, the degree of branching, the average chain length, the phosphate content, the gelatinization behavior, and the size and/or shape of the starch granule (starch granule morphology). Owing to an increase in the activity of the proteins according to the invention, for example by overexpressing suitable nucleic acid molecules, or by providing mutants which are no longer subject to the homologous regulatory mechanisms and/or have different temperature dependences with regard to their activities, it is possible to increase the yield in suitably genetically engineered plants.

The economic importance of the possibility of engaging in starch synthesis even only in maize is obvious: maize is the most important starch plant worldwide.

Approximately 80% of the starch produced worldwide each year is obtained from maize.

Thus, it is possible to express the nucleic acid molecules according to the invention in plant cells in order to increase the activity of the starch synthase in question. It is furthermore possible to modify the nucleic acid molecules according to the invention by methods known to the skilled worker in order to obtain starch synthases according to the invention which are no longer subject to the homologous regulatory mechanisms or show altered temperature dependences or substrate or product specificities.

When expressing the nucleic acid molecules according to the invention in plants, it is possible, in principle, for the protein synthesized to be localized in any compartment of the plant cell. To achieve localization in a particular compartment, the sequence which ensures localization in plastids must be deleted and, if appropriate, the remaining coding region linked to DNA sequences which ensure localization in the compartment in question. Such sequences are known (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106). Examples of plastid signal sequences have already been mentioned above in a different context.

The present invention thus also relates to transgenic plant cells which have been transformed with a nucleic acid molecule according to the invention or a vector according to the invention, and to transgenic plant cells derived from such transformed cells. Such cells contain a nucleic acid molecule according to the invention, the nucleic acid molecule preferably being linked to regulatory DNA elements which ensure transcription in plant cells, in particular to a promoter. A multiplicity of techniques are available for introducing DNA into a plant host cell. These techniques encompass the transformation of plant cells with T-DNA using *Agrobacterium tumefaciens* or *Agrobacterium rhizogenes* as transformation means, the transformation of protoplasts by means of polyethylene glycol, the injection, the electroporation of DNA, the introduction of DNA by means of the biolistic approach, and other possibilities.

The use of the agrobacteria-mediated transformation of plant cells has been researched into intensively and described sufficiently in EP-A2-0120516; Hoekema, in: The Binary Plant Vector System, Offsetdrukkerij Kanters B. V., Alblasserdam (1985), Chapter V; Fraley et al., Crit. Rev. Plant Sci. 4–46 and An et al. EMBO J. 4, (1985), 277–287. For the transformation of potato, see, for example, Rocha-Sosa et al. (EMBO J. 8, (1989), 29–33.).

The transformation of monocotyledonous plants by means of Agrobacterium-based vectors has also been described (Chan et al., Plant Mol. Biol. 22, (1993), 491–506; Hiei et al., Plant J. 6, (1994) 271–282; Deng et al, Science in China 33, (1990), 28–34; Wilmink et al., Plant Cell Reports 11, (1992), 76–80; May et al., Bio/Technology 13, (1995), 486–492; Conner and Domisse, Int. J. Plant Sci. 153 (1992), 550–555; Ritchie et al, Transgenic Res. 2, (1993), 252–265). An alternative system for the transformation of monocotyledonous plants is the transformation by the biolistic approach (Wan and Lemaux, Plant Physiol. 104, (1994), 37–48; Vasil et al., Bio/Technology 11 (1993), 1553–1558; Ritala et al., Plant Mol. Biol. 24, (1994), 317–325; Spencer et al., Theor. Appl. Genet. 79, (1990), 625–631), protoplast transformation, the electroporation of partially permeabilized cells, and the introduction of DNA by means of glass fibers. The transformation of maize, in particular, has been described repeatedly in the literature (cf., for example, WO 9506128A2, EP-A2-0513849, EP-A1-0465875, EP-A1-292435; Fromm et al., Biotechnology 8, (1990), 833–844; Gordon-Kamm et al., Plant Cell 2, (1990), 603–618; Koziel et al., Biotechnology 11 (1993), 194–200; Moroc et al., Theor. Appl. Genet. 80, (1990), 721–726).

The successful transformation of other cereal species has also been described, for example in the case of barley (Wan and Lemaux, see above; Ritala et al., see above; Krens et al., Nature 296, (1982), 72–74) and wheat (Nehra et al., Plant J. 5, (1994), 285–297).

Regulatory elements for the expression in plant cells of the nucleic acid molecules according to the invention are, in principle, any promoter, enhancer, terminator etc. which is active in plant cells. The promoter can be chosen in such a way that expression in the plants according to the invention is constitutive, or only in a particular tissue, at a particular point in time of the plant's development, or at a point in time determined by external factors. Relative to the plant, the promoter may be homologous or heterologous.

Examples of suitable promoters are the promoter of the cauliflower mosaic virus 35S RNA (see, for example, U.S. Pat. No. 5,352,605) and the Ubiquitin promoter (see, for example, U.S. Pat. No. 5,614,399) for constitutive expression, the patatin gene promoter B33 (Rocha-Sosa et al., EMBO J. 8 (1989), 23–29) for tuber-specific expression in potatoes, or a promoter which ensures expression only in photosynthetically active tissues, for example the ST-LS1 promoter (Stockhaus et al., Proc. Natl. Acad. Sci. USA 84 (1987), 7943–7947; Stockhaus et al., EMBO J. 8 (1989), 2445–2451), the Ca/b promoter (see, for example, U.S. Pat. No. 5,656,496, U.S. Pat. No. 5,639,952, Bansal et al., Proc. Natl. Acad. Sci. USA 89, (1992), 3654–3658) and the Rubisco SSU promoter (see, for example, U.S. Pat. No. 5,034,322, U.S. Pat. No. 4,962,028). However, it is also possible to use promoters which are only activated at a point in time which is determined by external factors (see, for example, WO9307279A1). Promoters of heat shock proteins, which permit simple induction, may be of particular interest in this context. Furthermore, seed-specific promoters such as, for example, the Vicia faba USP promoter, ensure seed-specific expression in Vicia faba and other plants (Fiedler et al., Plant Mol. Biol. 22, (1993), 669–679; Bäumlein et al., Mol. Gen. Genet. 225, (1991), 459–467). Other promoters which can be employed are fruit-specific promoters, for example as described in WO9101373A1.

Promoters which are especially preferably used are those for endosperm-specific expression such as, for example, the glutelin promoter (Leisy et al., Plant Mol. Biol. 14, (1990), 41–50; Zheng et al., Plant J. 4, (1993), 357–366), the wheat HMG promoter, the USP promoter, the phaseolin promoter, or promoters of maize zein genes (Pedersen et al., Cell 29, (1982), 1015–1026; Quatroccio et al., Plant Mol. Biol. 15 (1990), 81–93). It is possible with the aid of endosperm-specific promoters to increase the transcript quantity of the nucleic acid molecules according to the invention in the endosperm in comparison with the endosperm of corresponding wild-type plants.

The maize shrunken-1 promoter (sh-1) (Werr et al., EMBO J. 4, (1985), 1373–1380) is especially preferably used.

A termination sequence which serves for the correct transcriptional termination and for adding a poly-A tail to the transcript, which is understood to have a function in stabilizing the transcripts, may furthermore be present. Such elements have been described in the literature (cf., for example, Gielen et al., EMBO J. 8 (1989), 23–29) and are freely exchangeable.

In addition it is possible to generate, with the aid of the nucleic acid molecules according to the invention, plant cells and plants in which the activity of a protein according to the invention is reduced. This leads to the synthesis of the starch with altered chemical and/or physical properties in comparison with starch from wild-type plant cells.

Another subject matter of the invention are therefore also transgenic plant cells in which the activity of a protein according to the invention is reduced in comparison with corresponding non-genetically-modified plant cells of wild-type plants.

The term "wild-type plant"/"wild-type plant cell" means for the purposes of the present invention that these are plant/plant cells which acted as starting material for generating the plants/plant cells according to the invention, i.e. whose genetic information corresponds to that of a plant/plant cell according to the invention apart from the genetic modification which has been introduced.

For example, plant cells with a reduced activity of a protein according to the invention can successfully be generated by expressing a corresponding antisense RNA, or by expressing a suitably constructed ribozyme which specifically cleaves transcripts which encode one of the proteins according to the invention. Moreover, a reduced activity can be achieved by introducing those DNA molecules which, via a cosuppression effect, result in a reduced expression of endogenous genes which encode a protein according to the invention. Moreover, plant cells with a reduced activity of a protein according to the invention can be generated by means of in-vivo mutagenesis. To this end, mutations or insertions can be introduced, via homologous recombination, into an endogenous gene which encodes the protein according to the invention. The mutation or insertion leads to a reduced expression of the endogenous gene which encodes a protein according to the invention, or to the synthesis of an inactive protein according to the invention.

To reduce the activity of a protein according to the invention in plant cells, it is preferred to express an antisense RNA.

To this end, it is possible to use, on the one hand, DNA molecules which encompass the entire sequence encoding a protein according to the invention inclusive of any flanking sequences which are present, and, on the other hand, DNA molecules which only encompass portions of the coding sequence, it being necessary for these portions to be long enough to cause an antisense effect in the cells. However, genomic DNA molecules which encode, for example, an intron, can furthermore also be used. In general, sequences up to a minimum length of 15 bp, preferably a length of 100–500 bp, may be used for an effective antisense inhibition, in particular sequences with a length of over 500 bp. As a rule, DNA molecules are used which are shorter than 5000 bp, preferably sequences which are shorter than 2500 bp. DNA molecules which are homologous with regard to the plant species to be transformed are preferably used.

It is also possible to use DNA sequences which show a high degree of homology to the sequences of the DNA molecules according to the invention, but are not fully identical. The minimum homology should exceed approx. 65%. The use of sequences with homologies of between 95 and 100% is to be preferred.

Alternatively, a reduced activity of the protein according to the invention in the plant cells can also be achieved by a cosuppression effect. The method is known to the skilled worker and described, for example, by Jorgensen (Trends Biotechnol. 8 (1990), 340–344), Niebel et al., (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621) and in other sources.

Again, as in the case of the above-described antisense technology, DNA molecules can be used in this context which encompass the entire coding region of the nucleic acid molecule according to the invention or else DNA molecules which only encompass portions of the coding sequence. The use of introns is also feasible.

The expression of ribozymes for reducing the activity of certain enzymes in cells is known to the skilled worker and described, for example, in EP-B1-0321201. The expression of ribozymes in plant cells was described, for example, by Feyter et al. (Mol. Gen. Genet. 250, (1996), 329–338).

Furthermore, a reduced activity in plant cells of the nucleic acid molecule according to the invention may also be achieved by "in-vivo mutagenesis", where a chimeric RNA-DNA-oligonucleotide ("chimeroplast") is introduced into cells by transforming cells (Kipp, P. B. et al., Poster Session at the 5th International Congress of Plant Molecular Biology, Sep. 21–27, 1997, Singapore; R. A. Dixon and C. J. Arntzen, Meeting report on "Metabolic Engineering in Transgenic Plants", Keystone Symposia, Copper Mountain, Colo., USA, TIBTECH 15, (1997), 441–447; International Patent Application WO 9515972A1; Kren et al., Hepatology 25, (1997), 1462–1468; Cole-Strauss et al., Science 273, (1996), 1386–1389).

A portion of the DNA component of the RNA-DNA oligonucleotide is homologous to a nucleic acid sequence of an endogenous gene encoding a nucleic acid molecule according to the invention, but has, in comparison with the nucleic acid sequence of the endogenous gene, a mutation or contains a heterologous region surrounded by the homologous regions.

Base pairing of the homologous regions of the RNA-DNA oligonucleotide and of the endogenous nucleic acid molecule followed by homologous recombination allows the mutation, or heterologous region, present in the DNA component of the RNA-DNA oligonucleotide to be transferred into the endogenous gene of a plant cell. This leads to a reduced activity of a protein according to the invention.

The skilled worker furthermore knows that the activity of a protein according to the invention can be achieved by expressing non-functional derivatives, in particular transdominant mutants, of such proteins and/or expressing antagonists/inhibitors of such proteins. Antagonists/inhibitors of such proteins include, for example, antibodies, antibody fragments or molecules with similar binding properties. For example, a cytoplasmic scFv antibody was used for modulating the activity of the phytochrome A protein in genetically modified tobacco plants (Owen, Bio/Technology 10, (1992), 790–794; Review: Franken, E., Teuschel, U. and Hain, R., Current Opinion in Biotechnology 8, (1997), 411–416; Whitelam, Trends Plant Sci. 1, (1996), 268–272).

The term "reduced activity" means for the purposes of the present invention a reduced expression of endogenous genes which encode a protein according to the invention and/or a reduced quantity of protein according to the invention in the cells, in particular a reduced enzymatic activity of the protein according to the invention in the cells.

Reduced expression can be established, for example, by measuring the quantity of transcripts encoding the protein according to the invention, for example by Northern blot analysis. "Reduced" preferably means in this context that the amount of transcript compared with corresponding non-genetically-modified cells is reduced by at least 50%, preferably by at least 70%, especially preferably by at least 85% and very especially preferably by at least 95%.

The reduced amount of protein according to the invention can be determined, for example, by Western Blot analysis. "Reduced" preferably means in this context that the amount of protein according to the invention compared with corresponding, non-genetically-modified cells is reduced by at least 50%, preferably by at least 70%, especially preferably by at least 85% and very especially preferably by at least 95%. The reduced enzymatic activity of the protein according to the invention can be determined, for example, as described by Denyer und Smith (Planta 186 (1992), 609–617). A reduced enzymatic activity compared with corresponding, non-genetically-modified cells preferably means in this context a reduction by at least 50%, preferably by at least 70%, especially preferably by at least 85% and very especially preferably by at least 95%.

What has been said above in a different context about the term "genetically modified" also applies here.

Subject matter of the present invention are therefore in particular also transgenic plant cells.
  a) which contain at least one DNA molecule which can lead to the synthesis of at least one antisense RNA which causes a reduced expression of endogenous genes which encode a protein according to the invention;
  b) which contain at least one DNA molecule which, via a cosuppression effect, leads to a reduced expression of endogenous genes which encode a protein according to the invention;
  c) which contain at least one DNA molecule which leads to the synthesis of at least one ribozyme which specifically cleaves transcripts of endogenous genes which encode a protein according to the invention; and/or
  d) which, owing to an in-vivo mutagenesis, have a mutation or an insertion of a heterologous DNA sequence in at least one endogenous gene encoding a protein according to the invention, the mutation or insertion causing reduced expression of the gene or the synthesis of an inactive protein according to the invention.

It is furthermore possible, with the aid of the nucleic acid molecules according to the invention, to generate plant cells and plants in which the activity of a protein according to the invention is increased. This leads to the synthesis of a starch of altered chemical and/or physical properties compared with starch from wild-type plant cells and wild-type plants.

Another subject matter of the invention are also transgenic plant cells in which the activity of a protein according to the invention is increased by comparison with corresponding, non-genetically-modified plant cells of wild-type plants.

To generate plant cells according to the invention which have an increased activity of the protein according to the invention compared with corresponding, non-genetically-wild-type plant cells, nucleic acid molecules according to the invention are used, in sense orientation, which comprise the coding region of a starch synthase according to the invention. In a further embodiment, it is also possible to use portions of the coding region, under the condition that they encode a catalytically active starch synthase protein. In an especially preferred embodiment, the nucleic acid molecules indicated under Seq ID No. 1 are used.

The term "increased activity" means for the purposes of the present invention increased expression of endogenous genes which encode a protein according to the invention and/or an increased quantity of protein according to the invention in the cells, in particular an increased enzymatic activity of the protein according to the invention in the cells.

The increased expression can be determined, for example, by measuring the amount of the transcripts encoding the protein according to the invention, for example by Northern blot analysis. "Increased" in this context preferably means that the amount of transcripts compared with corresponding non-genetically modified cells is increased by at least 50%, preferably by at least 100%, in particular by at least 500% and especially preferably by at least 1500%.

The increased amount of protein according to the invention can be determined, for example, by Western blot analysis. "Increased" preferably means in this context that the amount of protein according to the invention compared with corresponding non-genetically modified cells is increased by at least 50%, preferably by at least 100%, in particular by at least 500% and especially preferably by at least 1500%.

The increased enzymatic activity of the protein according to the invention can especially preferably be determined as described by Denyer and Smith (see above). An increased enzymatic activity compared with corresponding, non-genetically-modified cells preferably means in this context an increase by at least 50%, preferably by at least 100%, in particular by at least 500%, and especially preferably by at least 1500%.

In a preferred embodiment of the invention, the transgenic plant cells according to the invention with increased activity of a protein according to the invention compared with plant cells from wild-type plants are those plant cells which originate from starch-storing tissues, preferably from tubers and the endosperm, in particular the endosperm of maize plants.

Surprisingly, it has been found that plant cells in which the activity of the protein according to the invention, in particular in plant cells of the endosperm, is increased compared with corresponding wild-type plants, synthesize a starch whose physicochemical properties are altered compared with starch synthesized in wild-type plants, in particular in the endosperm, so that it is better suited for specific purposes.

The plant cells according to the invention may belong to any plant species, i.e. to monocotyledonous or else dicotyledonous plants. They are preferably plant cells from agriculturally useful plants, i.e. plants which are grown by man for the purposes of nutrition or for technical, in particular industrial, purposes. The invention preferably relates to fiber-forming (for example flax, hemp, cotton), oil-storing (for example oilseed rape, sunflowers, soya beans), sugar-storing (for example sugar beet, sugar cane, sugar millet, banana) and protein-storing plants (for example legumes). In a further preferred embodiment, the invention relates to plant cells from fodder plants (for example grasses used as animal feed, fodder grasses, alfalfa, clover and the like), vegetable plants (for example tomatoes, lettuce, chicory).

In an especially preferred embodiment, the invention relates to plant cells from starch-storing plants (for example wheat, barley, oats, rye, potatoes, maize, rice, peas, cassava, mung bean), particularly preferred are plant cells from maize, rice, wheat and potatoes.

The plant cells according to the invention can be used for regenerating intact plants. The plants obtainable by regenerating the transgenic plant cells according to the invention are also a subject matter of the present invention.

Subject matter of the invention are furthermore plants which contain the above-described plant cells according to the invention. The plants according to the invention may be, in principle, plants of any plant species, i.e. both monocotyledonous or dicotyledonous plants. They are preferably plant cells from agriculturally useful plants, i.e. plants which are grown by man for the purposes of nutrition or for technical, in particular industrial, fibre-forming purposes. The invention preferably relates to plant cells from (for example flax, hemp, cotton), oil-storing (for example oilseed rape, sunflowers, soya beans), sugar-storing (for example sugar beet, sugar cane, sugar millet, banana) and protein-storing plants (for example legumes).

In a further preferred embodiment, the invention relates to fodder plants (for example grasses used as animal feed, fodder grasses, alfalfa, clover and the like), vegetable plants (for example tomatoes, lettuce, chicory).

In an especially preferred embodiment, the invention relates to starch-storing plants (for example wheat, barley, oats, rye, potatoes, maize, rice, peas, cassava, mung bean), particularly preferred are maize, rice, wheat and potato plants.

In further preferred embodiment, the plants according to the invention show an increased activity of a protein according to the invention in plant cells of starch-storing tissues compared with corresponding non-genetically-modified plant cells from wild-type plants, preferably in plant cells from tubers or the endosperm, especially preferably in plant cells of the endosperm of maize plants.

In a further embodiment of the invention, plants which contain the plant cells according to the invention with increased activity of the protein according to the invention, exhibit a higher yield and/or higher starch content compared with non-modified wild-type plants.

The term "higher yield" preferably means in this context an increased production of constituents, in particular starch, and/or biomass, in particular when the latter is measured by the fresh weight per plant.

The term "increased starch content" means in this context that the starch content in plant cells according to the invention is at least 10%, preferably at least 20%, in particular at least 30% and especially preferably at least 40% higher compared with plant cells of the non-modified wild-type plants.

Methods for determining the starch content are known to the skilled worker.

Such an increase in yield and/or starch content preferably relates to harvestable plant organs such as seeds, fruits, storage roots, tubers, roots, flowers, buds, shoots, stems or timber.

In accordance with the invention, the increase in yield amounts to at least 3% based on the biomass and/or constituents, compared with corresponding, non-transformed plants of the same genotype when these plants are grown under the same conditions, preferably at least 5%, in particular at least 10% and especially preferably at least 20% or even 40% compared with wild-type plants.

The present invention also relates to methods for generating transgenic plants, where a) a plant cell is subjected to genetic modification by introducing a nucleic acid molecule according to the invention and/or a vector according to the invention; and b) a plant is regenerated from a cell; and, if appropriate, c) more plants are generated from the plant of b)

What has already been explained above in a different context also applies to the genetic modification introduced as described in step a). For example, genetically modified plant cells show a reduced activity of the protein according to the invention or an increased activity of the protein according to the invention.

Plants may be regenerated in accordance with step b) by methods known to the skilled worker.

More plants may be generated in accordance with step c) of the methods according to the invention for example by vegetative propagation (for example using cuttings, tubers or by means of callus culture and regeneration of intact plants) or by generative propagation. Generative propagation is preferably done under controlled conditions, i.e. selected plants with specific properties are crossed with each other and propagated.

The present invention also relates to the plants obtainable by the methods according to the invention.

The present invention also relates to propagation material of plants according to the invention and of the transgenic plants generated in accordance with the methods according to the invention. The term propagation material encompasses those parts of the plant which are suitable for generating progeny by the vegetative or generative route. Examples which are suitable for vegetative propagation are cuttings, callus cultures, rhizomes or tubers. Other propagation material encompasses, for example, fruits, seeds, seedlings, protoplasts, cell cultures and the like. The propagation material is preferably tubers and seeds.

In a further embodiment, the present invention relates to harvestable plant organs of plants according to the invention such as fruits, storage roots, roots, flowers, buds, shoots or stems, preferably seeds or tubers, and to feedstuffs which contain these harvestable plant organs, preferably seeds or tubers. Harvestable plant organs according to the invention, preferably seeds or tubers and/or feedstuffs, may be characterized by an altered energy value, preferably an increased energy value.

The term "energy value" is to be understood as meaning in the present context in particular "digestible energy". The term "digestible energy" is defined as: digestible energy= feed gross energy minus fecal calorific value (Landwirtschaftliches Lehrbuch 2: Tierzucht [Textbook of Agriculture 2: animal production], Ed.:D. Schmidt, 5th Edition, 1982, Eugen Ulmer GmbH & Co, p. 244). Gross energy is to be understood as meaning the total calorific value of a feedstuff which can be measured in Joule. Methods for determining the "energy value" or the "digestible energy" are known to the skilled worker.

In accordance with the invention, the energy value is increased by at least 3%, preferably at least 10%, in particular at least 30% and especially preferably at least 60%.

Owing to the expression, or additional expression, of a nucleic acid molecule according to the invention and/or owing to the increased or reduced activity of a protein according to the invention, the transgenic plant cells and plants according to the invention synthesize a starch which is altered compared with starch synthesized in wild-type plants for example with regard to its physicochemical properties, in particular the amylose/amylopectin ratio, the degree of branching, the mean chain length, the phosphate content, the gelatinization behavior, the starch granule size and/or the starch granule shape. In particular, such a starch may be altered compared with wild-type starch with regard to the viscosity and/or the gelling properties of sizes of this starch.

Subject matter of the present invention is also the starch obtainable from the transgenic plant cells according to the invention and/or the plants according to the invention and/or the propagation material according to the invention.

Owing to the altered physicochemical properties, the starches according to the invention show altered functional properties. Important functional properties of starch, or its aqueous solutions, are the retrogradation behavior, the film-forming properties, the gel strength, the viscosity, the stability with regard to color, the enzymatic digestibility, the freeze-thaw stability, the stability to acids, the shear stability, the transparency, the water-binding capacity, the gelatinization properties and binding and adhesive properties. The starches according to the invention can be modified by processes known to the skilled worker and are suitable, in their unmodified or modified forms, for a variety of applications in the food or non-food sector.

In principle, the possible uses of the starch can be divided into two important sectors. One sector encompasses the hydrolysis products of the starch, mainly glucose and glucan units, which are obtained by enzymatic or chemical methods. They are used as starting materials for other chemical modifications and processes such as fermentation. Of importance here for reducing the outlay is the simplicity and inexpensive design of a hydrolysis process. Currently it is performed essentially enzymatically using amyloglucosidase. What would be feasible is a financial saving by using fewer enzymes. This could be caused by altering the structure of the starch, for example by increasing the granule surface area, better degradability owing to a lower degree of branching, or a sterical structure which limits the accessibility for the enzymes employed. The other sector in which starch, owing to its polymeric structure, is used is as a so-called native starch can be divided into two further fields of application:

1. The Food Industry

Starch is a traditional additive to a large number of foodstuffs in which its function is essentially to bind aqueous additives or to cause an increased viscosity or else increased gelling. Important characteristics are the flowing behavior sorptive behavior, the swelling temperature, the gelatinization temperature, the viscosity, the thickening power, starch solubility, transparency, gel structure, thermal stability, shear stability, stability to acids, the tendency to undergo retrogradation, the film-forming capacity, the freeze-thaw stability, digestibility and the ability of forming complexes with, for example, inorganic or organic ions.

2. The Non-food Industry

In this important sector, starch is employed as auxiliary for various production processes or as an additive in industrial products. When using starch as an auxiliary, mention must be made, in particular, of the paper and board industry. Starch acts mainly for retardation purposes (retaining solids), binding filler particles and fines, as a stiffener and for dehydration. Moreover, the advantageous properties of starch regarding stiffness, rigidity, sound, touch, luster, smoothness, bonding strength and the surfaces is exploited.

2.1 Paper and Board Industry

Within the papermaking process, four fields of application must be distinguished, i.e. surface, coating, stock and spraying.

The demands on starch with regard to surface treatment are essentially high whiteness, an adapted viscosity, highly stable viscosity, good film formation and low dust formation. When used for coating, the solids content, a suitable viscosity, a high binding capacity and a high pigment affinity play an important role. Of importance when used as additive to the stock is rapid, uniform, loss-free distribution, high mechanical strength and complete retention in the paper web. If the starch is used in the spraying sector, again, an adapted solids content, high viscosity and a high binding capacity are of importance.

2.2 The Adhesives Industry

An important field of application for starches is the adhesives industry, where the potential uses can be divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch-based adhesives are employed in the sectors production of corrugated board, production of paper sacks and bags, production of composite materials for paper and aluminum, production of box board and gumming adhesive for envelopes, stamps and the like.

2.3 Textile Industry and Textile Care Products Industry

An important field of application for starches as auxiliaries and additives is the sector production of textiles and textile care products. The following four fields of application must be distinguished within the textile industry: the use of starch as sizing agent, i.e. as auxiliary for smoothing and for strengthening smoothing behavior as a protection from the tensile forces applied during weaving, and for increasing resistance to abrasion during weaving, starch as a textile finishing agent, in particular after quality-reducing pretreatments such as bleaching, dyeing and the like, starch as thickener in the preparation of dye pastes for preventing bleeding, and starch as additive to glazing agents for sewing threads.

2.4 Construction Materials Industry

The fourth field of application is the use of starches as additives in construction materials. An example is the production of gypsum plasterboards, where the starch which is admixed to the gypsum slurry gelatinizes with the water, diffuses to the surface of the plaster core and there binds the board to the core. Other fields of application are the mixture to rendering and mineral fibers. In the case of ready-mixed concrete, starch products are employed for delaying binding.

2.5 Soil Stabilization

A further market for starch products is the production of soil stabilizers which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6 Use in Crop Protection Products and Fertilizers

One field of application for using starch is in crop protection products for altering the specific properties of the products. Thus, starches are employed for improving the wettability of crop protection products and fertilizers, for the controlled release of the active ingredients, for converting liquid active ingredients, volatile active ingredients and/or active ingredients with an offensive odor into microcrystalline, stable, shapeable substances, for mixing incompatible compounds and for extending the duration of action by reducing decomposition.

2.7 Pharmaceuticals, Medicine and the Cosmetics Industry

Another field of application is the sector of the pharmaceuticals, medicine and cosmetics industry. In the pharmaceuticals industry, starches are employed as binders for tablets or for diluting the binder in capsules. Moreover, starches are used as disintegrants for tablets since they absorb fluids after having been swallowed and swell within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8 Addition of Starch to Coal and Briquettes

A field of application for starch is as an additive to coal and briquettes. With an addition of starch, coal can be agglomerated, or briquetted, in terms of high quantity, thus preventing early decomposition of the briquettes. In the case of barbecue coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9 Ore Slick and Coal Silt Treatment

Furthermore, starch can be employed as flocculent in the treatment of ore slicks and coal silts.

2.10 Foundry Auxiliary

A further field of application is as additive to foundry auxiliaries. Various casting processes require cores made with sands treated with binders. The binder which is predominantly employed nowadays is bentonite, which is treated with modified starches, in most cases swellable starches.

The purpose of adding starch is to increase flowability and to improve binding power. In addition, the swellable starches can meet other demands of production engineering, such as being cold-water-dispersible, rehydratable, readily miscible with sand and having high water-binding capacity.

2.11 Use in the Rubber Industry

In the rubber industry, starch can be employed for improving the technical and visual quality. The reasons are the improvement of the surface luster, the improvement of handle and of appearance, and to this end starches scattered to the tacky gummed surfaces of rubber materials prior to cold curing, and also the improvement of the rubber's printability.

2.12 Production of Leather Substitutes

Modified starches may furthermore also be sold for the production of leather substitutes.

2.13 Starch in Synthetic Polymers

In the polymer sector, the following fields of application can be envisaged: the use of starch degradation products in the processing process (starch is only a filler, there is no direct bond between synthetic polymer and starch), or, alternatively, the use of starch degradation products in the production of polymers (starch and polymer form a stable bond).

The use of starch as a pure filler is not competitive in comparison with other substances such as talc. However, this is different when the specific properties of starch make an impact and thus markedly alter the spectrum of characteristics of the end products. An example of this is the use of starch products in the processing of thermoplastics, such as polyethylene. Here, the starch and the synthetic polymer are combined by coexpression in a ratio of 1:1 to give a masterbatch, from which various products are produced together with granulated polyethylene, using conventional process techniques. By using starch in polyethylene films, an increased substance permeability in the case of hollow bodies, an improved permeability for water vapor, an improved antistatic behavior, an improved antiblock behavior and an improved printability with aqueous inks can be achieved.

Another possibility is the use of starch in polyurethane foams. By adapting the starch derivatives and by process-engineering optimization, it is possible to control the reaction between synthetic polymers and the starches' hydroxyl groups in a directed manner. This results in polyurethane films which have the following spectrum of properties, owing to the use of starch: a reduced heat extension coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens and reduced aging. Disadvantages which still exist are a reduced printability and a reduced impact strength.

Product development is currently no longer restricted to films. Solid polymer products such as pots, slabs and dishes which contain a starch content of over 50% may also be produced. Moreover, starch/polymer mixtures are considered advantageous since their biodegradability is much higher.

Starch graft polymers become exceedingly important owing to their extremely high water binding capacity. They are products with a starch backbone and a side chain of a synthetic monomer, grafted on following the principle of the free-radical chain mechanism. The starch graft polymers which are currently available are distinguished by better binding and retention capacity of up to 1000 g of water per g of starch combined with high viscosity. The fields of application for these superabsorbers have extended greatly in recent years and are, in the hygiene sector, the products diapers and pads and, in the agricultural sector, for example seed coatings.

What is decisive for the application of novel, genetically engineered starches are, on the one hand, structure, water content, protein content, lipid content, fiber content, ash/phosphate content, amylose/amylopectin ratio, molecular mass distribution, degree of branching, granule size and granule shape and crystallization, and, on the other hand, also the characteristics which affect the following features: flowing behavior, sorptive behavior, gelatinization temperature, viscosity, thickening power, solubility, gel structure and transparency, heat stability, shear stability, stability to acids, tendency to undergo retrogradation, gel formation, freeze-thaw stability, complex formation, iodine binding, film formation, adhesive power, enzyme stability, digestibility and reactivity.

The production of modified starches by means of genetic engineering methods can, on the one hand, alter the properties of the starch derived from the plant in such a way that other modifications by means of chemical of physical alterations are no longer required. On the other hand, starches which have been altered by genetic engineering methods may be subjected to further chemical and/or physical modification, which leads to further improvement in quality for some of the above-described fields of application. These chemical and physical modifications are known in principle. They are, in particular, modifications by:

thermal treatment, treatment with acids, production of starch ethers starch alkyl ethers, O-allyl ethers, hydroxyalkyl ethers, O-carboxymethyl ethers, N-containing starch ethers, P-containing starch ethers, S-containing starch ethers production of crosslinked starches production of starch graft polymers oxidation and esterifications which lead to the formation of phosphate, nitrate, sulfate, xanthate, acetate and citrate starches. Other organic acids can also be used for the esterification.

The present invention furthermore relates to a process for the production of a modified starch comprising the step of extracting the starch from an above-described plant (plant cell) according to the invention and/or from starch-storing parts of such a plant. Such a process preferably also comprises the step of harvesting the plants which have been grown, and/or starch-storing parts of these plants before extracting the starch, and especially preferably furthermore the step of growing plants according to the invention prior to harvesting. Methods for extracting the starch from plants or from starch-storing parts of plants are known to the skilled worker.

Moreover, methods for extracting the starch from various starch-storing plants are described, for example, in "Starch: Chemistry and Technology (Editor: Whistler, BeMiller and Paschall (1994), 2nd Edition, Academic Press Inc. London Ltd; ISBN 0-12-746270-8; see, for example, Chapter XII, page 412–468: maize and sorghum starches: production; by Watson; Chapter XIII, page 469–479: tapioca, arrowroot and sago starches: production; by Corbishley and Miller; Chapter XIV, page 479–490: potato starch: production and uses; by Mitch; Chapter XV, page 491 to 506: wheat starch: production, modification and uses; by Knight and Oson; and Chapter XVI, page 507 to 528: rice starch: production and uses; by Rohmer and Klem; maize starch: Eckhoff et al., Cereal Chem. 73 (1996) 54–57, the extraction of maize starch on an industrial scale is generally done by wet milling.). Apparatus usually used in processes for extracting starch from plant materials are separators, decanters, hydrocyclones, spray dryers and fluidized-bed dryers.

Subject matter of the present invention is furthermore starch obtainable by the above-described process according to the invention.

The invention furthermore relates to starch obtainable from the plant cells according to the invention and/or plants according to the invention and to starch obtainable from starch-storing tissues, in particular tubers and kernels, of plants according to the invention.

In a further embodiment, the present invention relates to the use of the starches according to the invention in the industrial sector, preferably for the production of foodstuffs, feedstuffs and paper.

BRIEF DESCRIPTION OF THE DRAWINGS

FIG. 1: Plasmid map IR 65/87

LB: T-DNA left border

35S-T: 35S terminator (Frank et al., Cell 21, (1980), 285–294)

PAT: phosphinothricin resistance, EP-A2-0275957

35S-P: CaMV 35 S promoter (Frank et al., Cell 21, (1980), 285–294)

Ubiquitin P: ubiquitin promoter (Christensen et al., Plant Mol. Biol. 18, (1992), 675–689)

Ubi. intron: ubiquitin intron (Christensen et al., Plant Mol. Biol. 18, (1992), 675–689)

SS6: coding region of the nucleotide sequence indicated under SEQ ID No. 1 NOS: nos terminator (Depicker et al., J. Mol. Appl. Genet. 1, (1982), 561–573)

RB: T-DNA right border

Ampicillin: ampicillin resistance gene (Yanisch-Perron et al., Gene 33, (1985), 103–119)

Media and solutions used in the examples:

| | |
|---|---|
| 20 x SSC | 175.3 g NaCl |
| | 88.2 g sodium citrate |
| | twice-distilled H$_2$O to 1000 ml |
| | pH 7.0 with 10 N NaOH |
| YT | 8 g Bacto yeast extract |
| | 5 g Bacto typtone |
| | 5 g NaCl |
| | twice-distilled H$_2$O to 1000 ml |

Protoplast isolation medium (100 ml)

| | |
|---|---|
| Cellulase Onozuka R S (Meiji Seika, Japan) | 800 mg |
| Pectolyase Y 23 | 40 mg |
| KNO$_3$ | 200 mg |
| KH$_2$PO$_4$ | 136 mg |
| K$_2$HPO$_4$ | 47 mg |
| CaCl$_2$ 2H$_2$O | 147 mg |
| MgSO$_4$ 7H$_2$O | 250 mg |
| Bovine serum albumin (BSA) | 20 mg |
| Glucose | 4000 mg |
| Fructose | 4000 mg |
| Sucrose | 1000 mg |
| pH | 5.8 |
| Osmolarity | 660 mosm |

Protoplast wash solution 1: as protoplast isolation solution, but without cellulase, pectolyase and BSA

| transformation buffer | | | |
|---|---|---|---|
| a) | Glucose | 0.5 | M |
| | MES | 0.1 | % |
| | MgCl$_2$ 6H$_2$O | 25 | mM |
| | pH | 5.8 | |
| | bring to 600 mosm | | |
| b) | PEG 6000 solution | 0.5 | M |
| | Glucose | 100 | mM |
| | MgCl$_2$ 6H$_2$O | 100 | mM |
| | Hepes | 20 | mM |
| | pH | 6.5 | |

PEG 6000 is added to the above buffer under b) shortly before the solution is used (PEG 40% by weight). The solution is filtered through a 0.45 μm sterile filter.

| W5 solution | |
|---|---|
| CaCl$_2$ | 125 mM |
| NaCl | 150 mM |
| KCl | 5 mM |
| Glucose | 50 mM |

Protoplast culture medium (data in mg/l)

| | |
|---|---|
| KNO$_3$ | 3000 |
| (NH$_4$)$_2$SO$_4$ | 500 |
| MgSO$_4$ 7H$_2$O | 350 |
| KH$_2$PO$_4$ | 400 |
| CaCl$_2$ 2H$_2$O | 300 |

Fe-EDTA and trace elements as for Murashige-Skoog medium (Physiol. Plant, 15 (1962), 473).

| | |
|---|---|
| m-Inositol | 100 |
| Thiamine HCl | 1.0 |
| Nicotinamide | 0.5 |
| Pyridoxine HCl | 0.5 |
| Glycine | 2.0 |
| Glucuronic acid | 750 |
| Galacturoic acid | 750 |
| Galactose | 500 |
| Maltose | 500 |
| Glucose | 36,000 |
| Fructose | 36,000 |
| Sucrose | 30,000 |
| Asparagine | 500 |
| Glutamine | 100 |
| Proline | 300 |
| Casein hydrolyzate | 500 |
| 2,4-Dichlorophenoxyacetic acid (2,4-D) | 0.5 |
| pH | 5.8 |
| Osmolarity | 600 mosm |

The following methods are used in the examples:

1. Transformation of Maize (a) Preparation of Protoplasts of Cell Line DSM 6009

Protoplast Isolation

2–4 days, preferably 3 days, after the last medium change in a protoplast suspension culture, the liquid medium is pipetted off and the cells which remain are washed with 50 ml protoplast wash solution 1 and again dried by pipetting off the wash solution. 10 ml of protoplast isolation medium are added to in each case 2 g of the cell biomass harvested. The resuspended cells and cell aggregates are incubated in the dark for 4 to 6 hours at 27±2° C., with gentle shaking (30 to 40 rpm).

Protoplast Purification

As soon as at least 1 million protoplasts/ml have been released (observation under the microscope), the suspension is passed through a stainless-steel screen and a nylon screen of 200 and 45 μm mesh size, respectively. The combination of a 100 μm and a 60 μm screen is equally suitable for removing the cell aggregates. The protoplast-containing filtrate is assessed under the microscope. Usually, it contains 98–99% protoplasts. The remainder are undigested single cells. Protoplast preparations of this degree of purity are used for transformation experiments without additional gradient centrifugation. The protoplasts are sedimented by centrifugation (100 rpm in the swing-bucket rotor (100×g, 3 min). The supernatant is discarded and the protoplasts are resuspended in wash solution 1. The centrifugation step is repeated and the protoplasts are then resuspended in the transformation buffer.

(b) Protoplast Transformation

The protoplasts resuspended in transformation buffer are filled in 10 ml portions into 50 ml polyallomer tubes at a titer of 0.5–1×10$^6$ protoplasts/ml. The DNA used for the transformation is dissolved in Tris-EDTA (TE) buffer. 20 μg of plasmid DNA are added per ml of protoplast suspension. The vector used is a plasmid which mediates resistance to phosphinothricin (cf., for example, EP-A2-0513 849). After addition of the DNA, the protoplast suspension is shaken carefully to distribute DNA homogeneously in the solution. Immediately thereafter, 5 ml of PEG solution are added dropwise.

The PEG solution is distributed homogeneously by carefully turning the tubes. Then, another 5 ml of PEG solution are added and the mixing step to achieve homogeneity is repeated. The protoplasts remain in the PEG solution for 20 minutes at 25±2° C. Then the protoplasts are sedimented by centrifuging for 3 minutes (100 g; 1000 rpm). The supernatant is discarded. The protoplasts are washed by carefully shaking them in 20 ml of W5 solution, whereupon they are recentrifuged. Then they are resuspended in 20 ml of protoplast culture medium, recentrifuged and resuspended again in culture medium. The titer is brought to 6–8×10$^5$ protoplasts/ml, and the protoplasts are cultured in 3 ml portions in Petri dishes (ø 60 mm, height 15 mm). The Petri dishes are sealed with Parafilm and then placed in the dark at 25±2° C.

(c) Protoplast Culture

During the first 2–3 weeks after isolation and transformation, the protoplasts are cultured without addition of fresh medium. Once the cells regenerated from the protoplasts have developed into cell aggregates of over 20–50 cells, 1 ml of fresh protoplast culture medium which contains sucrose (90 g/l) as osmotic is added.

(d) Selection of Transformed Maize Cells, and Plant Regeneration

3–10 days after the addition of fresh medium, the cell aggregates which have formed from protoplasts can be plated out on agar media supplemented with 100 mg/l L-phosphinothricin. N6 medium with the vitamins of the protoplast culture medium, 90 g/l sucrose and 1.0 mg/l 2,4-D is equally suitable as an analogous medium, for example with the macro- and microelements of the MS medium (Murashige and Skoog (1962), see above).

The calli originating from stably transformed protoplasts can continue growing unimpeded on the selective medium. After 3–5 weeks, preferably 4 weeks, the transgenic calli can be transferred to fresh selection medium which also contains 100 mg/l L-phosphinothricin, but which no longer contains any auxin. In the course of 3–5 weeks, approx. 50% of the transgenic maize calli which have the L-phosphinothricin acetyl transferase gene integrated into their genome differentiate the first plants on this medium in the presence of L-phosphinothricin.

(e) Growing Transgenic Regenerated Plants

The embryogenic transformed maize tissue is grown on hormone-free N6 medium (Chu C.C. et al., Sci. Sin. 16 (1975), 659) in the presence of $5 \times 10^{-4}$ M L-phosphinothricin. On this medium, maize embryos which sufficiently express the phosphinothricin acetal transferase gene (PAT gene) develop into plants. Untransformed embryos, or those whose PAT activity is only very weak, die. As soon as the leaves of the in-vitro plants have reached a length of 4–6 cm, they can be transferred to soil. After agar residues are washed off the roots, the plants are planted into a 3:1:1:1 mixture of loam, sand, vermiculite and standard soil and adapted to the soil culture during the first 3 days after transplanting at a relative atmospheric humidity of 90–100%. They are grown on in a controlled-environment cabinet with a 14-hour-photoperiod, approx. 25,000 Lux at plant level, at a day/night temperature of $23\pm1/17\pm1°$ C. The adapted plants are grown at an atmospheric humidity of $65\pm5\%$.

4. Radiolabeling of DNA Fragments

DNA fragments were radiolabeled with the aid of a DNA Random Primer Labeling Kit by Boehringer (Germany) following the manufacturer's instructions.

The examples which follow illustrate the invention without imposing any form of limitation:

EXAMPLE 1

Identification, Isolation and Characterization of a cDNA Encoding a New Isoform of a *Zea mays* Starch Synthase To identify a cDNA encoding a new isoform of *Zea mays* starch synthase, total RNA was first isolated from maize kernels (15 to 20 days after pollination) following the method of Logemann et al. (Anal. Biochem. 163, (1987), 21–26). Then, 1 mg of total RNA was used to prepare poly A+-RNA using the Oligotex-mRNA purification kit (Quiagen) following the manufacturer's instructions.

Starting from 5 µg of poly A+-RNA, a cDNA library was then constructed with the aid of the ZAP cDNA synthesis kit by Stratagene. The library contained approx. $9 \times 10^5$ independent recombinant phages with an average cDNA insert size of approx. 1.3 kb.

Then plaque-lifting was carried out on approx. $4 \times 10^5$ phages. To do this, Hybond N filters (Amersham) were used. After prehybridization for 4 hours at 42° C. in buffer A (5×SSC, 0.5% BSA, 5×Denhardt, 1% SDS, 40 mM phosphate buffer, pH 7.2; 100 mg/l herring sperm DNA, 25% formamide), the filters were hybridized with a radiolabeled (Random Primed DNA Labeling Kit, Boehringer Mannheim) EcoRI/XhoI fragment (total cDNA) of the Solanum tuberosum SSIII cDNA (GenBank Acc. No. X 94400). After 12 hours, the filters were washed three times for 20 minutes at 55° C. in a buffer containing 3×SSC, 0.5% SDS. Then, an X-ray film was superimposed for approx. 14 hours.

Strongly hybridizing plaques were isolated, diluted, replaced and transferred to filters. These were again hybridized and washed as described above. After the isolated phages had been excised in-vivo following the manufacturer's instructions (Stratagene), various plasmids were isolated which were characterized by means of a restriction analysis. Then the DNA sequences of the plasmids which had the longest cDNA insertions were determined. One of these plasmids, which was termed pZm_SS6, contained the nucleotide sequence indicated in SEQ ID No. 1.

EXAMPLE 2

Generation of a Vector for Transforming Plants

Starting from a NotI/Bsp 120 1 fragment of plasmid pZm_SS6 which contains the complete coding region of the nucleotide sequence indicated under SEQ ID No. 1, vector IR65/87 (see FIG. 1), which is suitable, inter alia, for generating transgenic maize plants which have an increased activity (overexpression batch) or a reduced activity (cosuppression batch) of the starch synthase according to the invention, was generated by standard methods and deposited at the Deutsche Sammlung für Mikroorganismen on Aug. 5, 1999, with the deposit number DSM 12970. Vector IR65/87 was used for transforming maize plants in accordance with the above-described methods.

Then transgenic plants were selected which exhibited either increased activity or a reduced activity of the protein according to the invention compared with corresponding untransformed maize plants.

I claim:

1. An isolated nucleic acid molecule encoding a protein with the bioactivity of a starch synthase selected from the group consisting of
   (a) nucleic acid molecules which encode a protein with the amino acid sequence indicated under SEQ ID No. 2;
   (b) nucleic acid molecules which encompass the nucleotide sequence shown under SEQ ID No. 1 or a complementary sequence thereof;
   (c) nucleic acid molecules which encompass the coding region of the nucleotide sequence of the cDNA present in plasmid IR 65/87 (deposit number DSM 12970) or a complementary sequence thereof;
   (d) nucleic acid molecules whose nucleotide sequence deviates from the sequence of the nucleic acid molecules mentioned under (a), (b) or (c) owing to the degeneracy of the genetic code;
   (e) nucleic acid molecules which have over 85% sequence identity with SEQ ID NO:1; and
   (f) nucleic acid molecules which constitute allelic variants of the nucleic acid molecules indicated under (a), (b), (c), (d) or (e).

2. The nucleic acid molecule as claimed in claim 1 which is a DNA molecule.

3. The nucleic acid molecule as claimed in claim 1 which is an RNA molecule.

4. A vector comprising a nucleic acid molecule as claimed in claim 1.

5. The vector as claimed in claim 4 comprising one or more regulatory elements which ensure the transcription of said nucleic acid molecules and/or the synthesis of a translatable RNA in a pro- and/or eukaryotic cell.

6. The vector as claimed in claim 4, wherein said nucleic acid molecule is linked in sense orientation to regulatory elements which ensure the transcription and synthesis of a translatable RNA in pro- and/or eukaryotic cells, or wherein said nucleic acid molecule is linked in anti-sense orientation to regulatory elements which ensure the transcription and synthesis of a non-translatable RNA in pro- and/or eukaryotic cells.

7. A host cell which is transformed with a nucleic acid molecule as claimed in claim 1 or a vector as claimed in claim 4, or a cell which is derived from the host cell and which comprises the vector of claim 4.

8. The host cell as claimed in claim 7 which is a plant cell.

9. A method for producing a protein encoded by the nucleic acid molecule of claim 1, in which a host cell as claimed in claim 7 is cultured under conditions which permit the synthesis of the protein, and the protein is isolated from the cultured cells and/or the culture medium.

10. The plant cell of claim 8, wherein said nucleic acid molecule which encodes a protein with the bioactivity of a starch synthase is under the control of regulatory elements which permit the transcription of a translatable mRNA in plant cells.

11. The plant cell of claim 8, wherein the activity of a protein encoded by the nucleic acid molecule of claim 1 is increased in this plant cell compared with corresponding, non-genetically-modified plant cells from wild-type plants.

12. A plant comprising plant cells as claimed in claim 8.

13. The plant as claimed in claim 12 which is a crop plant.

14. The plant as claimed in claim 12 which is a starch-storing plant.

15. The plant as claimed in claim 12 which is a maize plant.

16. A method for generating a transgenic plant cell, wherein a plant cell is subjected to genetic modification by introducing a nucleic acid molecule as claimed in claim 1 and/or a vector as claimed in claim 4.

17. A method for generating a transgenic plant, wherein
   (a) a plant cell is subjected to genetic modification by introducing a nucleic acid molecule as claimed in claim 1 and/or a vector as claimed in claim 4; and
   (b) a plant is regenerated from this cell; and, if appropriate,
   (c) more plants are generated from the plant of (b).

18. Propagation material of a plant comprising plant cells as claimed in claim 8.

19. A method for producing a modified starch obtained from the host cell of claim 8, from the plant of claim 12, or from the propagation material of 18, comprising the step of extracting the starch from a plant cell as claimed in claim 8, from a plant as claimed in claim 12 and/or from propagation material as claimed in claim 18.

* * * * *

SEQUENCE LISTING

```
<160> NUMBER OF SEQ ID NOS:   29

<210> SEQ ID NO 1
<211> LENGTH: 4121
<212> TYPE: DNA
<213> ORGANISM: Zea mays
<220> FEATURE:
<221> NAME/KEY: CDS
<222> LOCATION: (442)..(3954)

<400> SEQUENCE: 1
gaattcggca cgagccgctt tggatccacc tctctgcgcg cggggccgcg cctgcacttc         60
```

```
gcacagtggc aggcggcagc ccccaacgcc atccacacat cccccggcaa atccttacc    120 caccgaaaaa agggaaaaat ggaggcaggc aggcggcact gcggcagtca cacatgcgca    180
cgggcacggt aaaagtacga gccaccttt ccctctcgat cgagcggccg aggaggagga    240
gagcctctct gtctctggcg aggggcgact gggcgagcgc ttcgtctaga cagcccagct    300
gcgcatttgg atgcaaatta cgtgtggagg atggagtaaa atactgagca agggagaggg    360
aagaggagac ggtctttct tttcttgagc cgaggagggg gatcaggtgg agtgagcgag    420
```

| | | | |
|---|---|---|---|
| ggggaggttt tgccgccggc a atg gag atg aat ctc cgg gcg gag agc cca | | | 471 |
| Met Glu Met Asn Leu Arg Ala Glu Ser Pro | | | |
| 1       5          10 | | | |

| ctc tgc tcc cgg ggc cgc ccc gcc ctc gtc gtg cgc ccg gcc gct gca | 519 |
|---|---|
| Leu Cys Ser Arg Gly Arg Pro Ala Leu Val Val Arg Pro Ala Ala Ala | |
| 15          20          25 | |

| gcc act ggc ctc gcg ctg tct gtc gta agg tgc agc aga ttt acg aga | 567 |
|---|---|
| Ala Thr Gly Leu Ala Leu Ser Val Val Arg Cys Ser Arg Phe Thr Arg | |
| 30          35          40 | |

| ggc ggg ctc gtt cga tgc atg gta tca agt tca gat tat ccc aag agg | 615 |
|---|---|
| Gly Gly Leu Val Arg Cys Met Val Ser Ser Asp Tyr Pro Lys Arg | |
| 45          50          55 | |

| aat ccg agg agg gca tcg act tct aag agc aag ggc gtt gcc tct gga | 663 |
|---|---|
| Asn Pro Arg Arg Ala Ser Thr Ser Lys Ser Lys Gly Val Ala Ser Gly | |
| 60          65          70 | |

| ggg tat gct tcg aga cct act gct gaa tcc agt acg aag aag ata gaa | 711 |
|---|---|
| Gly Tyr Ala Ser Arg Pro Thr Ala Glu Ser Ser Thr Lys Lys Ile Glu | |
| 75          80          85          90 | |

| cag agc agg aac aat gaa ggt gat ttc agc aga gcc aat ggg tca ctc | 759 |
|---|---|
| Gln Ser Arg Asn Asn Glu Gly Asp Phe Ser Arg Ala Asn Gly Ser Leu | |
| 95          100          105 | |

| tat ggc gag gca gca gag cag gca agt act gct gaa gaa tcg tct cag | 807 |
|---|---|
| Tyr Gly Glu Ala Ala Glu Gln Ala Ser Thr Ala Glu Glu Ser Ser Gln | |
| 110          115          120 | |

| gtt tac atg aca gga gac att tta agt ggc gca gaa agg gac gga gct | 855 |
|---|---|
| Val Tyr Met Thr Gly Asp Ile Leu Ser Gly Ala Glu Arg Asp Gly Ala | |
| 125          130          135 | |

| ggt acc gaa gaa gag gct gac caa aat caa tct tca gcg ttg cct tcc | 903 |
|---|---|
| Gly Thr Glu Glu Glu Ala Asp Gln Asn Gln Ser Ser Ala Leu Pro Ser | |
| 140          145          150 | |

| gcg tcc atg gat gat gac tca atc gac cgg caa ctt gat gag tac cgt | 951 |
|---|---|
| Ala Ser Met Asp Asp Asp Ser Ile Asp Arg Gln Leu Asp Glu Tyr Arg | |
| 155          160          165          170 | |

| ggt aaa ata agt gct cta gta agt tcc aaa cct gaa cct tcg tca ctt | 999 |
|---|---|
| Gly Lys Ile Ser Ala Leu Val Ser Ser Lys Pro Glu Pro Ser Ser Leu | |
| 175          180          185 | |

| gca agt gtt gct gga caa aac gaa tca gtt ggc ggt ttt cac ggc cag | 1047 |
|---|---|
| Ala Ser Val Ala Gly Gln Asn Glu Ser Val Gly Gly Phe His Gly Gln | |
| 190          195          200 | |

| cac gaa cca ata act ggt tct gag gaa cat ggc agt tca att gtt gat | 1095 |
|---|---|
| His Glu Pro Ile Thr Gly Ser Glu Glu His Gly Ser Ser Ile Val Asp | |
| 205          210          215 | |

| gca cca ata aaa ggc agg cta ttt gct gag gcc gtt gtg ggt cat aag | 1143 |
|---|---|
| Ala Pro Ile Lys Gly Arg Leu Phe Ala Glu Ala Val Val Gly His Lys | |
| 220          225          230 | |

| gat ttt act gaa tca gca gca gga aag gca agc agc gag aat gag gaa | 1191 |
|---|---|
| Asp Phe Thr Glu Ser Ala Ala Gly Lys Ala Ser Ser Glu Asn Glu Glu | |
| 235          240          245          250 | |

| ggg caa gct gtc tcg tta gaa gat gat gtc ggg ata agt aca gac gca | 1239 |
|---|---|
| Gly Gln Ala Val Ser Leu Glu Asp Asp Val Gly Ile Ser Thr Asp Ala | |
| 255          260          265 | |

-continued

| | |
|---|---|
| gat gaa gag ctt ccg gta tct gaa gat gat cca gaa gtg cta ctg agg<br>Asp Glu Glu Leu Pro Val Ser Glu Asp Asp Pro Glu Val Leu Leu Arg<br>270                         275                      280 | 1287 |
| agg ctt caa gag ctt gct gat gag aat tat tcg act ggg aac aac tgt<br>Arg Leu Gln Glu Leu Ala Asp Glu Asn Tyr Ser Thr Gly Asn Asn Cys<br>285                     290                   295 | 1335 |
| ttt gtt ttc cct gaa gta gtg aag gct gat tcg atg att gat ctt tac<br>Phe Val Phe Pro Glu Val Val Lys Ala Asp Ser Met Ile Asp Leu Tyr<br>300                       305                 310 | 1383 |
| tta aac cgc agc atg tcg gcc tta gct agt gag tcc gac gtt ttt gta<br>Leu Asn Arg Ser Met Ser Ala Leu Ala Ser Glu Ser Asp Val Phe Val<br>315                     320                   325                 330 | 1431 |
| aaa gga gca ttc aat ggt tgg aga tgg aac cgt ttc act gaa aca atg<br>Lys Gly Ala Phe Asn Gly Trp Arg Trp Asn Arg Phe Thr Glu Thr Met<br>335                     340                 345 | 1479 |
| cat aga agc gaa tta aga ggg gat tgg tgg tgc tgc aag ctc tac att<br>His Arg Ser Glu Leu Arg Gly Asp Trp Trp Cys Cys Lys Leu Tyr Ile<br>350                     355                   360 | 1527 |
| ccc aag cag gca tac aga cta gac ttt gta ttc ttt aac ggt gac act<br>Pro Lys Gln Ala Tyr Arg Leu Asp Phe Val Phe Phe Asn Gly Asp Thr<br>365                     370                 375 | 1575 |
| gtc tat gaa aat aac aat cac aac gat ttt ttc ctg gaa ata gaa agt<br>Val Tyr Glu Asn Asn Asn His Asn Asp Phe Phe Leu Glu Ile Glu Ser<br>380                       385                 390 | 1623 |
| gac ata gat gaa cac tca ttt gag gac ttc ttg gtt gaa gaa aag cga<br>Asp Ile Asp Glu His Ser Phe Glu Asp Phe Leu Val Glu Glu Lys Arg<br>395                       400                   405                 410 | 1671 |
| aag gaa ctc gag agg ctt gct gca gaa gaa gct gaa agg aaa aga caa<br>Lys Glu Leu Glu Arg Leu Ala Ala Glu Glu Ala Glu Arg Lys Arg Gln<br>415                     420                 425 | 1719 |
| gct gag gag cgg cac agg aga gag gaa gaa agg gcc gcg atg gaa gct<br>Ala Glu Glu Arg His Arg Arg Glu Glu Glu Arg Ala Ala Met Glu Ala<br>430                     435                 440 | 1767 |
| gac agg gca caa gca agg tct gag gtc gag atg aag aaa gag aaa ttg<br>Asp Arg Ala Gln Ala Arg Ser Glu Val Glu Met Lys Lys Glu Lys Leu<br>445                     450                 455 | 1815 |
| cgc cag atg ttg agt tcg gct agc aga tat gct gag aac tta tgg tac<br>Arg Gln Met Leu Ser Ser Ala Ser Arg Tyr Ala Glu Asn Leu Trp Tyr<br>460                     465                 470 | 1863 |
| ata gaa cct aac acc tac aga gga gga gac aga gtt aga ttg tac tat<br>Ile Glu Pro Asn Thr Tyr Arg Gly Gly Asp Arg Val Arg Leu Tyr Tyr<br>475                       480                 485                 490 | 1911 |
| aat aga agc tcg aga tca cta atg cat aac act gag att tgg atg cat<br>Asn Arg Ser Ser Arg Ser Leu Met His Asn Thr Glu Ile Trp Met His<br>495                     500                 505 | 1959 |
| gga ggt tat aac aac tgg att gat gga ctc tca ata gct gaa aga ctt<br>Gly Gly Tyr Asn Asn Trp Ile Asp Gly Leu Ser Ile Ala Glu Arg Leu<br>510                     515                 520 | 2007 |
| gtc aaa tct cat gaa aag gaa ggc gat tgg tgg tat gta gaa gtt aca<br>Val Lys Ser His Glu Lys Glu Gly Asp Trp Trp Tyr Val Glu Val Thr<br>525                     530                 535 | 2055 |
| tta cct gaa agg gca ttg gtg ttg gat tgg gtt ttt gct gat gga cca<br>Leu Pro Glu Arg Ala Leu Val Leu Asp Trp Val Phe Ala Asp Gly Pro<br>540                     545                 550 | 2103 |
| cct ggg aat gca agg aat tat gat aac aat gga agg cag gat ttt cat<br>Pro Gly Asn Ala Arg Asn Tyr Asp Asn Asn Gly Arg Gln Asp Phe His<br>555                     560                 565                 570 | 2151 |
| gcc atc gtt cct aat aac ata tcg gat gat atc ttt tgg gtg gaa gaa<br>Ala Ile Val Pro Asn Asn Ile Ser Asp Asp Ile Phe Trp Val Glu Glu<br>575                     580                 585 | 2199 |

```
gaa cat agg atc ttt aca agg ctt caa caa gag aga aga gaa agg gag    2247
Glu His Arg Ile Phe Thr Arg Leu Gln Gln Glu Arg Arg Glu Arg Glu
            590                 595                 600 agt gcc gaa aga ata aag gct gag aga tct gca aaa atg aag gct gag    2295
Ser Ala Glu Arg Ile Lys Ala Glu Arg Ser Ala Lys Met Lys Ala Glu
        605                 610                 615 atg aag gaa aag act atg aga gcg ttt ctg ctc tca caa aaa cat att    2343
Met Lys Glu Lys Thr Met Arg Ala Phe Leu Leu Ser Gln Lys His Ile
620                 625                 630 gtg tat act gag cca ctc gaa gta cgt gca gga acc act gtg gac gtt    2391
Val Tyr Thr Glu Pro Leu Glu Val Arg Ala Gly Thr Thr Val Asp Val
635                 640                 645                 650 ctt tat aat cct tct aac aca gtg ctg aat gga aag tca gag gtt tgg    2439
Leu Tyr Asn Pro Ser Asn Thr Val Leu Asn Gly Lys Ser Glu Val Trp
            655                 660                 665 ttc aga ggt tcc ttt aac cgt tgg act cat cca agt ggt ccc tta cca    2487
Phe Arg Gly Ser Phe Asn Arg Trp Thr His Pro Ser Gly Pro Leu Pro
            670                 675                 680 cca cag aag atg gta aag gct gag aat agt tca cac tta cga aca aca    2535
Pro Gln Lys Met Val Lys Ala Glu Asn Ser Ser His Leu Arg Thr Thr
        685                 690                 695 gtc agt gtt ccc ctg gat gca tat atg atg gac ttt gtt ttc tct gag    2583
Val Ser Val Pro Leu Asp Ala Tyr Met Met Asp Phe Val Phe Ser Glu
700                 705                 710 tcg gaa gaa ggt gga aga tat gac aat agg aac ggg atg gat tat cat    2631
Ser Glu Glu Gly Gly Arg Tyr Asp Asn Arg Asn Gly Met Asp Tyr His
715                 720                 725                 730 att cct gtg tct gat tcg gtt gca agg gaa cct cca atg cat att gta    2679
Ile Pro Val Ser Asp Ser Val Ala Arg Glu Pro Pro Met His Ile Val
            735                 740                 745 cac att gca gtg gaa atg gct cct atc gca aag gtt gga ggc ctt ggt    2727
His Ile Ala Val Glu Met Ala Pro Ile Ala Lys Val Gly Gly Leu Gly
            750                 755                 760 gat gtt gtt aca agc ctt tca cga gct gtt cag gat tta ggc cat aaa    2775
Asp Val Val Thr Ser Leu Ser Arg Ala Val Gln Asp Leu Gly His Lys
        765                 770                 775 gtt gag gtt att ctg ccg aag tat gat tgt tta atc cta agc agt gtg    2823
Val Glu Val Ile Leu Pro Lys Tyr Asp Cys Leu Ile Leu Ser Ser Val
780                 785                 790 aag gat tta cac tac caa caa agt ttt gct tcg ggt ggc aca gag gta    2871
Lys Asp Leu His Tyr Gln Gln Ser Phe Ala Ser Gly Gly Thr Glu Val
795                 800                 805                 810 aaa gta tgg ttt gga aag gtt gaa gat ctg cca gtt tac ttc ttg gaa    2919
Lys Val Trp Phe Gly Lys Val Glu Asp Leu Pro Val Tyr Phe Leu Glu
            815                 820                 825 cca caa aat ggc atg ttt tgg gtt gga tgt gtg tat ggg aag aat gat    2967
Pro Gln Asn Gly Met Phe Trp Val Gly Cys Val Tyr Gly Lys Asn Asp
            830                 835                 840 gag agt aga ttt ggc ttc ttc tgt cat tct gct ctg gag ttt ctg ctc    3015
Glu Ser Arg Phe Gly Phe Phe Cys His Ser Ala Leu Glu Phe Leu Leu
        845                 850                 855 caa aaa gga tct tct cct gat atc ata cat tgt cat gac tgg tca agt    3063
Gln Lys Gly Ser Ser Pro Asp Ile Ile His Cys His Asp Trp Ser Ser
860                 865                 870 gct ccc gtt gct tgg cta tac aag gaa cag tat gct ctt aat ggg ctg    3111
Ala Pro Val Ala Trp Leu Tyr Lys Glu Gln Tyr Ala Leu Asn Gly Leu
875                 880                 885                 890 gga aat ggt cgg att gta ttt acc atc cac aat ctt gag ttt gga gcg    3159
Gly Asn Gly Arg Ile Val Phe Thr Ile His Asn Leu Glu Phe Gly Ala
            895                 900                 905
```

```
cat cac att ggc aag gca atg gca cat tgt gac aag gct aca act gtc      3207
His His Ile Gly Lys Ala Met Ala His Cys Asp Lys Ala Thr Thr Val
            910                 915                 920 tct gat aca tat tca aag gaa gtg gct gga cat gga gct att gca cct      3255
Ser Asp Thr Tyr Ser Lys Glu Val Ala Gly His Gly Ala Ile Ala Pro
        925                 930                 935 cac tac tat aaa ttc cat gga att cga aat gga att gat cct gac att      3303
His Tyr Tyr Lys Phe His Gly Ile Arg Asn Gly Ile Asp Pro Asp Ile
    940                 945                 950 tgg gat cca tat act gac aga ttt att ccg gtt cat tat aca tca gag      3351
Trp Asp Pro Tyr Thr Asp Arg Phe Ile Pro Val His Tyr Thr Ser Glu
955                 960                 965                 970 aat gtt ctt gag ggc aag ggt gct gca aaa aag gca ttg cag cag atg      3399
Asn Val Leu Glu Gly Lys Gly Ala Ala Lys Lys Ala Leu Gln Gln Met
                975                 980                 985 ctt gga tta cag caa act gat agc cct gtt gtt gga atc atc act cgt      3447
Leu Gly Leu Gln Gln Thr Asp Ser Pro Val Val Gly Ile Ile Thr Arg
            990                 995                 1000 cta aca gtg cag aag gga atc cac ctt atc aaa cat gca atg cat cga      3495
Leu Thr Val Gln Lys Gly Ile His Leu Ile Lys His Ala Met His Arg
        1005                1010                1015 gct ctt gaa cgc aat ggg cag gtg gtt tta ctg ggt tct gca cca gat      3543
Ala Leu Glu Arg Asn Gly Gln Val Val Leu Leu Gly Ser Ala Pro Asp
    1020                1025                1030 cat cgc ata caa ggt gac ttt aca aat tta gcc agt aag ctg cat ggt      3591
His Arg Ile Gln Gly Asp Phe Thr Asn Leu Ala Ser Lys Leu His Gly
1035                1040                1045                1050 gaa tac cat ggc cgg gtg aag cta tgt tta acc tat gac gag cca ctg      3639
Glu Tyr His Gly Arg Val Lys Leu Cys Leu Thr Tyr Asp Glu Pro Leu
                1055                1060                1065 tca cat ttg ctt att gct atg cgc tac gga tcc atc ccg att gtt cgg      3687
Ser His Leu Leu Ile Ala Met Arg Tyr Gly Ser Ile Pro Ile Val Arg
            1070                1075                1080 aaa act gga ggc ctg tac gac acc gtc ttt gac gtc gac gat gat aag      3735
Lys Thr Gly Gly Leu Tyr Asp Thr Val Phe Asp Val Asp Asp Asp Lys
        1085                1090                1095 gat cgg gct caa gca caa ggc ctc gag cca aat gga ttc agt ttc gaa      3783
Asp Arg Ala Gln Ala Gln Gly Leu Glu Pro Asn Gly Phe Ser Phe Glu
    1100                1105                1110 gga gct gat agc agt ggt gta gat tat gct ctc gac aga gct ata acc      3831
Gly Ala Asp Ser Ser Gly Val Asp Tyr Ala Leu Asp Arg Ala Ile Thr
1115                1120                1125                1130 gcg ttt tat gat gcc cgc gac tgg ttc aac tcc ctt agc aag agg gta      3879
Ala Phe Tyr Asp Ala Arg Asp Trp Phe Asn Ser Leu Ser Lys Arg Val
                1135                1140                1145 atg gag caa gat tgg tca tgg aat aga cct gca cta gac tac atg gag      3927
Met Glu Gln Asp Trp Ser Trp Asn Arg Pro Ala Leu Asp Tyr Met Glu
            1150                1155                1160 ttg tac cat tct gct cgc aaa aac tga tacattttac cacaagggaa           3974
Leu Tyr His Ser Ala Arg Lys Asn
        1165                1170 aacaggccca gtttgcccag tttatgagca tctcagatgc aacacagagt gtatagttag    4034
agaatgccac ccgttgtacg ttactgccgt tacatgcatg tgtatacaca tctaaaaaaa    4094
aaaaaaaaaa aacggcacga gctcgtg                                        4121

<210> SEQ ID NO 2
<211> LENGTH: 1170
<212> TYPE: PRT
<213> ORGANISM: Zea mays
```

```
<400> SEQUENCE: 2

Met Glu Met Asn Leu Arg Ala Glu Ser Pro Leu Cys Ser Arg Gly Arg
 1               5                  10                  15

Pro Ala Leu Val Val Arg Pro Ala Ala Ala Thr Gly Leu Ala Leu
             20                  25                  30

Ser Val Val Arg Cys Ser Arg Phe Thr Arg Gly Gly Leu Val Arg Cys
             35                  40                  45

Met Val Ser Ser Ser Asp Tyr Pro Lys Arg Asn Pro Arg Arg Ala Ser
 50                  55                  60

Thr Ser Lys Ser Lys Gly Val Ala Ser Gly Gly Tyr Ala Ser Arg Pro
 65                  70                  75                  80

Thr Ala Glu Ser Ser Thr Lys Lys Ile Glu Gln Ser Arg Asn Asn Glu
                 85                  90                  95

Gly Asp Phe Ser Arg Ala Asn Gly Ser Leu Tyr Gly Glu Ala Ala Glu
                 100                 105                 110

Gln Ala Ser Thr Ala Glu Glu Ser Gln Val Tyr Met Thr Gly Asp
             115                 120                 125

Ile Leu Ser Gly Ala Glu Arg Asp Gly Ala Gly Thr Glu Glu Glu Ala
         130                 135                 140

Asp Gln Asn Gln Ser Ser Ala Leu Pro Ser Ala Ser Met Asp Asp
145                 150                 155                 160

Ser Ile Asp Arg Gln Leu Asp Glu Tyr Arg Gly Lys Ile Ser Ala Leu
                 165                 170                 175

Val Ser Ser Lys Pro Glu Pro Ser Ser Leu Ala Ser Val Ala Gly Gln
             180                 185                 190

Asn Glu Ser Val Gly Gly Phe His Gly Gln His Glu Pro Ile Thr Gly
             195                 200                 205

Ser Glu Glu His Gly Ser Ser Ile Val Asp Ala Pro Ile Lys Gly Arg
     210                 215                 220

Leu Phe Ala Glu Ala Val Val Gly His Lys Asp Phe Thr Glu Ser Ala
225                 230                 235                 240

Ala Gly Lys Ala Ser Ser Glu Asn Glu Glu Gly Gln Ala Val Ser Leu
                 245                 250                 255

Glu Asp Asp Val Gly Ile Ser Thr Asp Ala Asp Glu Glu Leu Pro Val
             260                 265                 270

Ser Glu Asp Asp Pro Glu Val Leu Leu Arg Arg Leu Gln Glu Leu Ala
     275                 280                 285

Asp Glu Asn Tyr Ser Thr Gly Asn Asn Cys Phe Val Phe Pro Glu Val
     290                 295                 300

Val Lys Ala Asp Ser Met Ile Asp Leu Tyr Leu Asn Arg Ser Met Ser
305                 310                 315                 320

Ala Leu Ala Ser Glu Ser Asp Val Phe Val Lys Gly Ala Phe Asn Gly
                 325                 330                 335

Trp Arg Trp Asn Arg Phe Thr Glu Thr Met His Arg Ser Glu Leu Arg
                 340                 345                 350

Gly Asp Trp Trp Cys Cys Lys Leu Tyr Ile Pro Lys Gln Ala Tyr Arg
             355                 360                 365

Leu Asp Phe Val Phe Asn Gly Asp Thr Val Tyr Glu Asn Asn
     370                 375                 380

His Asn Asp Phe Phe Leu Glu Ile Glu Ser Asp Ile Asp Glu His Ser
385                 390                 395                 400

Phe Glu Asp Phe Leu Val Glu Glu Lys Arg Lys Glu Leu Glu Arg Leu
                 405                 410                 415
```

-continued

```
Ala Ala Glu Glu Ala Glu Arg Lys Arg Gln Ala Glu Arg His Arg
            420                 425                 430

Arg Glu Glu Glu Arg Ala Ala Met Glu Ala Asp Arg Ala Gln Ala Arg
        435                 440                 445

Ser Glu Val Glu Met Lys Lys Glu Lys Leu Arg Gln Met Leu Ser Ser
    450                 455                 460

Ala Ser Arg Tyr Ala Glu Asn Leu Trp Tyr Ile Glu Pro Asn Thr Tyr
465                 470                 475                 480

Arg Gly Gly Asp Arg Val Arg Leu Tyr Tyr Asn Arg Ser Ser Arg Ser
                485                 490                 495

Leu Met His Asn Thr Glu Ile Trp Met His Gly Gly Tyr Asn Asn Trp
            500                 505                 510

Ile Asp Gly Leu Ser Ile Ala Glu Arg Leu Val Lys Ser His Glu Lys
        515                 520                 525

Glu Gly Asp Trp Trp Tyr Val Glu Val Thr Leu Pro Glu Arg Ala Leu
    530                 535                 540

Val Leu Asp Trp Val Phe Ala Asp Gly Pro Pro Gly Asn Ala Arg Asn
545                 550                 555                 560

Tyr Asp Asn Asn Gly Arg Gln Asp Phe His Ala Ile Val Pro Asn Asn
                565                 570                 575

Ile Ser Asp Asp Ile Phe Trp Val Glu Glu His Arg Ile Phe Thr
            580                 585                 590

Arg Leu Gln Gln Glu Arg Arg Glu Arg Glu Ser Ala Glu Arg Ile Lys
        595                 600                 605

Ala Glu Arg Ser Ala Lys Met Lys Ala Glu Met Lys Glu Lys Thr Met
    610                 615                 620

Arg Ala Phe Leu Leu Ser Gln Lys His Ile Val Tyr Thr Glu Pro Leu
625                 630                 635                 640

Glu Val Arg Ala Gly Thr Thr Val Asp Val Leu Tyr Asn Pro Ser Asn
                645                 650                 655

Thr Val Leu Asn Gly Lys Ser Glu Val Trp Phe Arg Gly Ser Phe Asn
            660                 665                 670

Arg Trp Thr His Pro Ser Gly Pro Leu Pro Pro Gln Lys Met Val Lys
        675                 680                 685

Ala Glu Asn Ser Ser His Leu Arg Thr Thr Val Ser Val Pro Leu Asp
    690                 695                 700

Ala Tyr Met Met Asp Phe Val Phe Ser Glu Ser Glu Gly Gly Arg
705                 710                 715                 720

Tyr Asp Asn Arg Asn Gly Met Asp Tyr His Ile Pro Val Ser Asp Ser
                725                 730                 735

Val Ala Arg Glu Pro Pro Met His Ile Val His Ile Ala Val Glu Met
            740                 745                 750

Ala Pro Ile Ala Lys Val Gly Gly Leu Gly Asp Val Val Thr Ser Leu
        755                 760                 765

Ser Arg Ala Val Gln Asp Leu Gly His Lys Val Glu Val Ile Leu Pro
    770                 775                 780

Lys Tyr Asp Cys Leu Ile Leu Ser Ser Val Lys Asp Leu His Tyr Gln
785                 790                 795                 800

Gln Ser Phe Ala Ser Gly Gly Thr Glu Val Lys Val Trp Phe Gly Lys
                805                 810                 815

Val Glu Asp Leu Pro Val Tyr Phe Leu Glu Pro Gln Asn Gly Met Phe
            820                 825                 830
```

-continued

```
Trp Val Gly Cys Val Tyr Gly Lys Asn Asp Glu Ser Arg Phe Gly Phe
            835                 840                 845

Phe Cys His Ser Ala Leu Glu Phe Leu Leu Gln Lys Gly Ser Ser Pro
    850                 855                 860

Asp Ile Ile His Cys His Asp Trp Ser Ser Ala Pro Val Ala Trp Leu
865                 870                 875                 880

Tyr Lys Glu Gln Tyr Ala Leu Asn Gly Leu Gly Asn Gly Arg Ile Val
                885                 890                 895

Phe Thr Ile His Asn Leu Glu Phe Gly Ala His His Ile Gly Lys Ala
                900                 905                 910

Met Ala His Cys Asp Lys Ala Thr Thr Val Ser Asp Thr Tyr Ser Lys
            915                 920                 925

Glu Val Ala Gly His Gly Ala Ile Ala Pro His Tyr Tyr Lys Phe His
        930                 935                 940

Gly Ile Arg Asn Gly Ile Asp Pro Asp Ile Trp Asp Pro Tyr Thr Asp
945                 950                 955                 960

Arg Phe Ile Pro Val His Tyr Thr Ser Glu Asn Val Leu Glu Gly Lys
                965                 970                 975

Gly Ala Ala Lys Lys Ala Leu Gln Gln Met Leu Gly Leu Gln Gln Thr
            980                 985                 990

Asp Ser Pro Val Val Gly Ile Ile Thr Arg Leu Thr Val Gln Lys Gly
        995                 1000                1005

Ile His Leu Ile Lys His Ala Met His Arg Ala Leu Glu Arg Asn Gly
1010                1015                1020

Gln Val Val Leu Leu Gly Ser Ala Pro Asp His Arg Ile Gln Gly Asp
1025                1030                1035                1040

Phe Thr Asn Leu Ala Ser Lys Leu His Gly Glu Tyr His Gly Arg Val
                1045                1050                1055

Lys Leu Cys Leu Thr Tyr Asp Glu Pro Leu Ser His Leu Leu Ile Ala
                1060                1065                1070

Met Arg Tyr Gly Ser Ile Pro Ile Val Arg Lys Thr Gly Gly Leu Tyr
            1075                1080                1085

Asp Thr Val Phe Asp Val Asp Asp Lys Asp Arg Ala Gln Ala Gln
        1090                1095                1100

Gly Leu Glu Pro Asn Gly Phe Ser Phe Glu Gly Ala Asp Ser Ser Gly
1105                1110                1115                1120

Val Asp Tyr Ala Leu Asp Arg Ala Ile Thr Ala Phe Tyr Asp Ala Arg
            1125                1130                1135

Asp Trp Phe Asn Ser Leu Ser Lys Arg Val Met Glu Gln Asp Trp Ser
            1140                1145                1150

Trp Asn Arg Pro Ala Leu Asp Tyr Met Glu Leu Tyr His Ser Ala Arg
            1155                1160                1165

Lys Asn
    1170

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 3

Ser His Thr Ile Tyr Ala Ala Ser Asp Leu Phe Ile Ile Pro Ser Ile
  1               5                   10                  15
```

```
Phe Glu Pro Cys Gly Leu Thr Gln Met Ile Ala Met Arg Tyr Gly Ser
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 4

Ser His Leu Ile Tyr Ala Gly Ala Asp Phe Ile Leu Val Pro Ser Ile
  1               5                  10                  15

Phe Glu Pro Cys Gly Leu Thr Gln Leu Thr Ala Met Arg Tyr Gly Ser
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 5

Ser His Leu Ile Tyr Ala Gly Ala Asp Phe Ile Leu Val Pro Ser Ile
  1               5                  10                  15

Phe Glu Pro Cys Gly Leu Thr Gln Leu Thr Ala Met Arg Tyr Gly Ser
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 6

Ala His Gln Met Met Ala Gly Ala Asp Val Leu Ala Val Thr Ser Arg
  1               5                  10                  15

Phe Glu Pro Cys Gly Leu Ile Gln Leu Gln Gly Met Arg Tyr Gly Thr
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 7

Ala His Gln Met Met Ala Gly Ala Asp Val Leu Ala Val Thr Ser Arg
  1               5                  10                  15

Phe Glu Pro Cys Gly Leu Ile Gln Leu Gln Gly Met Arg Tyr Gly Thr
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 8

Ala His Met Ile Thr Ala Gly Ala Asp Phe Met Leu Ile Pro Ser Arg
  1               5                  10                  15
```

```
Phe Glu Pro Cys Gly Leu Ile Gln Leu His Ala Met Arg Tyr Gly Thr
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 9

Ala His Met Ile Thr Ala Gly Ala Asp Phe Met Leu Val Pro Ser Arg
1               5                   10                  15

Phe Glu Pro Cys Gly Leu Ile Gln Leu His Ala Met Arg Tyr Gly Thr
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 10

Ala His Leu Ile Met Ala Gly Ala Asp Val Leu Ala Val Pro Ser Arg
1               5                   10                  15

Phe Glu Pro Cys Gly Leu Ile Gln Leu Gln Gly Met Arg Tyr Gly Thr
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 11

Ala His Lys Ile Ile Ala Gly Ala Asp Phe Ile Val Ile Pro Ser Arg
1               5                   10                  15

Phe Glu Pro Cys Gly Leu Val Gln Leu His Ala Met Pro Tyr Gly Thr
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 12

Ala His His Ile Met Ala Gly Ala Asp Leu Leu Ala Val Thr Ser Arg
1               5                   10                  15

Phe Glu Pro Cys Gly Leu Ile Gln Leu Gln Gly Met Arg Tyr Gly Thr
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 13

Ala His His Ile Met Ala Gly Ala Asp Val Leu Ala Val Thr Ser Arg
1               5                   10                  15
```

```
Phe Glu Pro Cys Gly Leu Ile Gln Leu Gln Gly Met Arg Tyr Gly Thr
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: motif VII

SEQUENCE: 14

Ser His Arg Ile Thr Ala Gly Cys Asp Ile Leu Leu Met Pro Ser Arg
  1               5                  10                  15

Phe Glu Pro Cys Gly Leu Asn Gln Leu Tyr Ala Met Gln Tyr Gly Thr
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 15

Ala His Arg Ile Thr Ala Gly Ser Asp Ile Leu Leu Met Pro Ser Arg
  1               5                  10                  15

Phe Glu Pro Cys Gly Leu Asn Gln Leu Tyr Ala Met Ser Tyr Gly Thr
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 16

Ser His Arg Ile Thr Ala Gly Cys Asp Ile Leu Leu Met Pro Ser Arg
  1               5                  10                  15

Phe Glu Pro Cys Gly Leu Asn Gln Leu Tyr Ala Met Arg Tyr Gly Thr
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 17

Ser His Arg Ile Thr Ala Gly Ala Asp Ile Leu Leu Met Pro Ser Arg
  1               5                  10                  15

Phe Glu Pro Cys Ala Leu Asn Gln Leu Tyr Ala Met Lys Tyr Gly Thr
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 18

Ala His Arg Ile Thr Ala Gly Ala Asp Ile Ala Leu Met Pro Ser Arg
  1               5                  10                  15
```

```
Phe Glu Pro Cys Gly Leu Asn Gln Leu Tyr Ala Met Ala Tyr Gly Thr
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 19

Ser His Arg Ile Thr Ala Gly Cys Asp Ile Leu Leu Met Pro Ser Arg
 1               5                  10                  15

Phe Glu Pro Cys Gly Leu Asn Gln Leu Tyr Ala Met Gln Tyr Gly Thr
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 20

Ser His Arg Ile Thr Ala Gly Cys Asp Ile Leu Leu Met Pro Ser Arg
 1               5                  10                  15

Phe Glu Pro Cys Gly Leu Asn Gln Leu Tyr Ala Met Gln Tyr Gly Thr
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 21

Ala His Arg Ile Thr Ala Gly Ala Asp Val Leu Val Met Pro Ser Arg
 1               5                  10                  15

Phe Glu Pro Cys Gly Leu Asn Gln Leu Tyr Ala Met Ala Tyr Gly Thr
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 22

Ala His Arg Ile Thr Ala Gly Ala Asp Ile Leu Leu Met Pro Ser Arg
 1               5                  10                  15

Phe Glu Pro Cys Gly Leu Asn Gln Leu Tyr Ala Met Ala Tyr Gly Thr
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 23

Ala Arg Lys Leu Tyr Ala Ser Ser Asp Phe Ile Leu Met Pro Ser Tyr
 1               5                  10                  15
```

```
Phe Glu Pro Cys Gly Leu Thr Gln Met Ile Gly Met Arg Tyr Gly Cys
            20                  25                  30
```

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 24

```
Ala His Gln Ile Tyr Ala Gly Ser Asp Met Phe Leu Met Pro Ser Lys
 1               5                  10                  15

Phe Glu Pro Cys Gly Leu Thr Gln Leu Tyr Ala Leu Arg Tyr Gly Cys
            20                  25                  30
```

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 25

```
Ala His Gln Ile Tyr Ala Gly Ala Asp Leu Phe Leu Ile Pro Ser Leu
 1               5                  10                  15

Phe Glu Pro Cys Gly Leu Ser Gln Met Ile Ala Leu Arg Tyr Gly Thr
            20                  25                  30
```

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 26

```
Ala His Gln Ile Tyr Ala Gly Ala Asp Leu Phe Leu Ile Pro Ser Leu
 1               5                  10                  15

Phe Glu Pro Cys Gly Leu Gly Gln Leu Ile Ala Leu Gln Tyr Gly Ala
            20                  25                  30
```

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 27

```
Ala His Gln Ile Tyr Ala Gly Ala Asp Leu Phe Leu Ile Pro Ser Leu
 1               5                  10                  15

Phe Glu Pro Cys Gly Leu Gly Gln Leu Ile Ala Leu Gln Tyr Gly Ala
            20                  25                  30
```

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 28

```
Ser His Leu Met Val Ala Gly Gly Asp Val Ile Leu Val Pro Ser Arg
 1               5                  10                  15
```

```
                                    -continued

Phe Glu Pro Cys Gly Leu Thr Gln Leu Tyr Gly Leu Gln Tyr Gly Thr
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: motif VII

<400> SEQUENCE: 29

Ala His Leu Ile Tyr Gly Ala Ala Asp Ile Ile Val Val Pro Ser Asn
 1               5                  10                  15

Tyr Glu Pro Cys Gly Leu Thr Gln Met Ile Gly Leu Arg Tyr Gly Ala
            20                  25                  30
```